United States Patent
Hansen et al.

(10) Patent No.: US 9,701,740 B2
(45) Date of Patent: Jul. 11, 2017

(54) CELL-PENETRATING ANTI-DNA ANTIBODIES AND USES THEREOF INHIBIT DNA REPAIR

(75) Inventors: James E. Hansen, Branford, CT (US); Peter M. Glazer, Guilford, CT (US); Richard H. Weisbart, Los Angeles, CA (US); Robert N. Nishimura, Santa Monica, CA (US); Grace Chan, Monterey Park, CA (US)

(73) Assignees: YALE UNIVERSITY, New Haven, CT (US); THE REGENTS OF THE UNIVERSITY OF CALIFORNIA, Oakland, CA (US); The United States of America represented by the Department of Veterans Affairs, Washington, DC (US)

( * ) Notice: Subject to any disclaimer, the term of this patent is extended or adjusted under 35 U.S.C. 154(b) by 42 days.

(21) Appl. No.: 14/009,327

(22) PCT Filed: Apr. 2, 2012

(86) PCT No.: PCT/US2012/031860
§ 371 (c)(1),
(2), (4) Date: Oct. 1, 2013

(87) PCT Pub. No.: WO2012/135831
PCT Pub. Date: Oct. 4, 2012

(65) Prior Publication Data
US 2014/0050723 A1    Feb. 20, 2014

Related U.S. Application Data

(60) Provisional application No. 61/470,918, filed on Apr. 1, 2011.

(51) Int. Cl.
| C07K 16/18 | (2006.01) |
| A61K 39/00 | (2006.01) |
| A61K 39/395 | (2006.01) |
| C07K 16/44 | (2006.01) |
| A61K 31/704 | (2006.01) |
| A61K 45/06 | (2006.01) |
| A61K 31/337 | (2006.01) |
| A61K 31/475 | (2006.01) |
| A61K 31/513 | (2006.01) |
| A61K 31/7068 | (2006.01) |
| A61K 33/24 | (2006.01) |

(52) U.S. Cl.
CPC ............ *C07K 16/18* (2013.01); *A61K 31/337* (2013.01); *A61K 31/475* (2013.01); *A61K 31/513* (2013.01); *A61K 31/704* (2013.01); *A61K 31/7068* (2013.01); *A61K 33/24* (2013.01); *A61K 39/39558* (2013.01); *A61K 45/06* (2013.01); *C07K 16/44* (2013.01); *A61K 2039/505* (2013.01); *C07K 2317/622* (2013.01); *C07K 2317/73* (2013.01); *C07K 2317/77* (2013.01)

(58) Field of Classification Search
None
See application file for complete search history.

(56) References Cited

U.S. PATENT DOCUMENTS

| 4,812,397 | A | 3/1989 | Weisbart | |
| 5,780,033 | A * | 7/1998 | Torchilin et al. ...... | C07K 16/30 424/138.1 |
| 7,189,396 | B1 * | 3/2007 | Weisbart ............... | 424/133.1 |
| 2002/0090608 | A1 | 7/2002 | Palese | |
| 2003/0083305 | A1 | 5/2003 | Palese | |
| 2003/0109475 | A1 | 6/2003 | Debs | |
| 2004/0033235 | A1 | 2/2004 | Bolognesi | |
| 2004/0052820 | A1 | 3/2004 | Bolognesi | |
| 2005/0003343 | A1 | 1/2005 | Palese | |
| 2005/0256073 | A1 | 11/2005 | Lipford | |
| 2006/0110740 | A1 | 5/2006 | Hurwitz | |
| 2006/0216701 | A1 | 9/2006 | Palese | |
| 2008/0004561 | A1 * | 1/2008 | Genkin et al. ............ | 604/5.02 |
| 2008/0292618 | A1 * | 11/2008 | Weisbart ............... | 424/130.1 |

(Continued)

FOREIGN PATENT DOCUMENTS

| EP | 1666055 | 6/2006 | |
| KR | WO 2009134027 A2 * | 11/2009 | ............ C07K 16/30 |

(Continued)

OTHER PUBLICATIONS

Pavlovic et al. (Autoimmune Diseases, 2010, 2010:1-18).*
Kozyr et al. (Immunology Letters, 2002, 80:41-47).*
Foroutan et al. (Archives of Iranian Medicin, 2011, 14:321-326; published Oct. 21, 2010).*
ATCC (ATCC_CCL-86_Raji, 2015).*
Gruhne et al. (Oncogene, 2009, 28:3997-4008).*
Fiorica (Gynecological Oncology, 2003, 90:S16-S21).*
(ATCC_COS7, 2015).*
Coffin (Science, 1995, 267:483-489).*
Stone et al. (Gastroenterology, 1993, 104:196-202, abstract).*
Kim et al. (The Journal of Biological Chemistry, 2006, 281:15287-15295).*

(Continued)

*Primary Examiner* — Julie Wu
(74) *Attorney, Agent, or Firm* — Pabst Patent Group LLP

(57) ABSTRACT

Antibodies that penetrate cell nuclei and inhibit DNA repair or interfere with DNA metabolism are provided for treatment of cancer (both directly and by sensitizing cancer cells to DNA-damaging treatments) or inhibiting or preventing viral infection, proliferation or metabolism. The method involves treating cells with a composition containing cell-penetrating anti-DNA antibodies or derivatives thereof, alone or in combination with treatment that induces DNA damage such as DNA-damaging chemotherapy or radiation. The impact of the cell-penetrating anti-DNA antibodies or derivatives thereof is potentiated in cancer cells that are deficient in DNA repair, and the cell-penetrating anti-DNA antibodies or derivatives thereof are synthetically lethal to cancer cells with DNA repair deficiencies.

32 Claims, 12 Drawing Sheets

(56) References Cited

U.S. PATENT DOCUMENTS

| | | |
|---|---|---|
| 2009/0028901 A1 | 1/2009 | Palese |
| 2009/0186337 A1 | 7/2009 | Eleouet |
| 2009/0186802 A1 | 7/2009 | Alluis |
| 2010/0143358 A1 | 6/2010 | Weisbart |
| 2010/0196993 A1 | 8/2010 | Nishimura |
| 2010/0311171 A1 | 12/2010 | Nakanishi |
| 2011/0300164 A1 | 12/2011 | Lipford |
| 2012/0010124 A9 | 1/2012 | Alluis |
| 2012/0214240 A1 | 8/2012 | Nakanishi |
| 2013/0137644 A1 | 5/2013 | Alluis |
| 2013/0266570 A1 | 10/2013 | Weisbart |
| 2014/0050723 A1 | 2/2014 | Hansen |
| 2014/0234309 A1 | 8/2014 | Nishimura |
| 2015/0376279 A1 | 12/2015 | Hansen |

FOREIGN PATENT DOCUMENTS

| | | |
|---|---|---|
| WO | 2008091911 | 7/2008 |
| WO | 2009134027 | 11/2009 |
| WO | 2012135831 | 10/2012 |
| WO | 2012145125 | 10/2012 |
| WO | 2015106290 | 7/2015 |
| WO | 2015134607 | 9/2015 |
| WO | 2016033321 | 3/2016 |
| WO | 2016033324 | 3/2016 |

OTHER PUBLICATIONS

Weisbart et al. (International Journal of Oncology, 2004, 25:1113-1118).*
Padlan (Advances in Protein Chemistry, 1996, 49:57-133).*
Corada (Blood, 2001; 97:1679-84).*
Tzartos et al., Methods in Molecular Biology, 1996, 66:55-66.*
Kulkarni-Kale et al. Nucleic Acid Research, 2005, 33:W168-W171.*
Eivazova et al. (Immunology, 2000, 101:371-377).*
Rivadeneyra-Espinoza et al. (Journal of Autoimmunity, 2006, 26:52-56).*
Berglund et al. (Protein Science, 2008, 17:606-613).*
Alarcon-Segovia, "Antinuclear antibodies: to penetrate or not to penetrate, that was the question", Lupus, 10:315-8 (2001).
Arnaudeau, et al., "DNA double-strand breaks associated with replication forks are predominantly repaired by homologous recombination involving an exchange mechanism in mammalian cells", J Mol Biol, 307:1235-45 (2001).
Bindra, et al., "Down-regulation of Rad51 and decreased homologous recombination in hypoxic cancer cells", Mol. Cell. Biol., 24(19):8504-18 (2004).
Bryant, et al., "Specific killing of BRCA2-deficient tumours with inhibitors of poly (ADP-ribose) polymerase", Nature, 434:913-7 (2005).
Chi, et al., "Roles of ATP binding and ATP hydrolysis in human Rad51 recombinase function", DNA Repair (Amst) 5:381-91 (2006).
Dray, et al., "Molecular basis for enhancement of the meiotic DMC1 recombinase by RAD51 associated protein 1 (RAD51AP1)", PNAS, 108:3560-5 (2011).
Farmer, et al., "Targeting the DNA repair defect in BRCA mutant cells as a therapeutic strategy", Nature 434:917-21 (2005).
Feng, et al., "Rad52 inactivation is synthetically lethal with BRCA2 deficiency", PNAS, 108:686-91 (2011).
Hansen, et al., "Antibody-mediated Hsp70 protein therapy", Brain Res., 1088 (1):187-96 (2006).
Hansen, et al., "Antibody-mediated p53 protein therapy prevents liver metastasis in vivo", Cancer Res., 67(4):1769-74 (2007a).
Hansen, et al., "Intranuclear protein transduction through a nucleoside salvage pathway", J Biol Chem., 282:20790-3 (2007b).
Jordan, et al., Mechanism of mitotic block and inhibition of cell proliferation by taxol at low concentrations, PNAS, 90:9552-6 (1993).

Kaelin, Jr., et al., "The concept of synthetic lethality in the context of anticancer therapy", Nat Rev Cancer, 5:689-98 (2005).
Lau, et al., "Suppression of HIV-1 infection by a small molecule inhibitor of the ATM kinase", Nat Cell Biol, 7(5): 493-500 (2005).
Li, et al., "Homologous recombination in DNA repair and DNA damage tolerance", Cell Res., 18:99-113 (2008).
Lisi, et al. "Advances in the understanding of the Fc gamma receptors-mediated autoantibodies uptake", Clin Exp Med 11:1-10 (2011).
Moynahan, et al., "BRCA2 is required for homology-directed repair of chromosomal breaks", Mol Cell, 7:263-72 (2001).
Sakai, et al., "Functional restoration of BRCA2 protein by secondary BRCA2 mutations in BRCA2-mutated ovarian carcinoma", Cancer Res., 69:6381-6 (2009).
Spertini, et al., "Idiotypic vaccination with a murine anti-dsDNA antibody: phase I study in patients with nonactive systemic lupus erythematosus with nephritis", J Rheumatol 269120:2602-8 (1999).
Stachelek, et al., "Potentiation of temozolomide cytotoxicity by inhibition of DNA polymerase beta is accentuated by BRCA2 mutation", Cancer Re.,s 70:409-17 (2010).
Sung, et at., "DNA strand exchange mediated by a RAD51-ssDNA nucleoprotein filament with polarity opposite to that of RecA", Cell, 82:453-61 (1995).
Sung, et al., "Rad51 recombinase and recombination mediators", J Biol. Chem., 278:42729-32 (2003).
Sung, "Catalysis of ATP-dependent homologous DNA pairing and strand exchange by yeast RAD51 protein", Science 265:1241-3 (1994).
Tewey, et al., "Adriamycin-induced DNA damage mediated by mammalian DNA topoisomerase II", Science 226:466-8 (1984).
Weisbart, et al., "A conserved anti-DNA antibody idiotype associated with nephritis in murine and human systemic lupus erythematosus", J Immunol 144 (7):2653-8 (1990).
Weisbart, et al., "Novel protein transfection of primary rat cortical neurons using an antibody that penetrates living cells", J Immunol., 164: 6020-6 (2000).
Xu, et al., "MCM10 mediates RECQ4 association with MCM2-7 helicase complex during DNA replication", EMBO J., 28:3005-14 (2009a).
Xu, et al., "Dual DNA unwinding activities of the Rothmund-Thomson syndrome protein, RECQ4", EMBO J 28:568-77 (2009b).
Yoder, et al., "The base excision repair pathway is required for efficient lentivirus integration", PLoS One, 6(3) e17862 (2011).
Zack, et al., "Mechanisms of cellular penetration and nuclear localization of an anti-double strand DNA autoantibody", J Immunol., 157:2082-8 (1996).
Zhan, et al., "Recombinant Fv-Hsp70 protein mediates neuroprotection after focal cerebral ischemia in rats", Stroke, 41(3):538-43 (2010).
Colburn, et al., "Anti-guanosine antibodies in murine and human lupus have the internal image of G-binding proteins", J Rheumatol., 30(5):993-7 (2003).
Colburn, et al., "Serum antibodies as a marker for SLE disease activity and pathogen potential", Clinica Chimica Acta, 370:9-16 (2006).
Gu, et al, "Genetic determinants of autoimmune disease abd coronary vasculitis in the MRL-lpr/lpr mouse model of systemic lupus erythematosus", J Immunol, 161:6999-7006 (1998).
Hansen, et al., "Targeting cancer with a lupus autoantibody", Sci Translational Med., 4(157):157ra142 (2012).
Itoh, et al., "Diagnostic use of anti-modified nucleoside monoclonal antibody", Tohoku J Exp Med., 168(2):329-31 (1992).
Lee, et al, "Gene silencing by cell-penetrating, sequence-selective and nucleic-acid hydrolyzing", Nucleic Acid Res., pp. 1-14 (2009).
Weisbart, et al., "A cell-penetrating bispecific antibody for therapeutic regulation of intracellular targets", Mol Cancer Ther., 11:2169 (2012).
Young, et al, "Targeting K-ras mutant cancer cells with a lupus anti-guanosine antibody", Proceedings: AACR Annual Meeting Apr. 5-9, San Diego, CA, Abstract Only (2014).
Achuthan, et al., "Drug-induced senescence generates chemoresistant stemlike cells with low reactive oxygen species", J. Biol. Chem., 286:37813-29 (2011).

(56) References Cited

OTHER PUBLICATIONS

Adjei, "Blocking oncogenic Ras signaling for cancer therapy", J Natl Cancer Inst., 93(14):1062-74 (2001).
American Cancer Society, Cancer Facts & Figures, pp. 1-70 (2014).
Barka, et al., "Transduction of TAT-HA—galactosidase Fusion Protein into Salivary Gland-derived Cells and Organ Cultures of the Developing Gland, and into RatSubmandibular Gland in Vivo", Histochem Cytochem., 48(11):1453-60 (2000).
Bassi, et al., "Nuclear PTEN controls DNA repair and sensitivity to genotoxic stress", Science, 341:395-9 (2013).
Bernatsky, et al., Breast, ovarian, and endometrial malignancies in systemic lupus erythematosus: a meta-analysis Br. J. Cancer 104:1478-81(2011a).
Bernatsky, et al., "Cancer risk in systemic lupus: an updated international multi-centre cohort study", J. Autoimmun. 42:130-5 (2013).
Bernatsky, et al., "Decreased breast cancer risk in systemic lupus erythematosus: the search for a genetic basis continues", Lupus, 21:896-9 (2008b).
Bernatsky, et al., "Prostate cancer in systemic lupus erythematosus", Int. J. Cancer, 129: 2966-9 (2011b).
Bernatsky, et al., "The relationship between cancer and medication exposures in systemic lupus erythaematosus: a case-cohort study", Ann. Rheum. Dis. 67:74-9 (2008).
Bitzer, et al., "Sendai virus vectors as an emerging negative-strand RNA viral vector system", J Gene Med., 5(7):543-53 (2003).
Celldex, "CDX-011 Clinical program", http://www.celldextherapeutics.com/wt/page/cds_011_breast?CMP=KNC-3G5620403736., retrieved from the interned Mar. 31, 2011.
Chan, et al., "Targeting cancer with a cell-penetrating anti-DNA antibody", J Investigative Med., 60(1):148 (2012).
Chothia and Lesk, "Canonical structures for the hypervariable regions of immunoglobulins", J Mol. Biol., 196:901-17 (1987).
Cleaver, et al., "Phosphorylated H2Ax is not an unambiguous marker for DNSA double-strand breaks", Cell Cycle, 10:3223-4 (2011).
Collingridge, et al., "Pentoxifylline improves the oxygenation and radiarion response of BA 1112 rat rhabdomyosarcomas and EMT6 mouse mammary carcinomas", Int J Cancer, 90(5):256-64 (2000).
Collins, et al., "Viral vectors in cancer immunotherapy: which vector for which strategy", Curr Gene Ther., 8(2):66-78 (2008).
Cuesta, et al., "Multivalent antibodies: when design surpasses evolution", Trends in Biotechnol., 28(7):355-62 (2010).
Dean, et al, "Current advances in the translation of cascular tissue engineering to the treatment of pediatric congenital heart disease", Yale J Biol Med, 85:229-38 (2012).
Derossi, et al., "The third helix of the Antennapedia homeodomain translocates through biological membranes", J. Biol. Chem. 269(14):10444-50 (1994).
Deyev, et al., "Multivalemcy: the hallmark of antibodies used for optimization of tumor targeting by design", Bioesseays, 30(9):904-18 (2008).
Dimri, et al., "A biomarker that identifies senescent human cells in culture and in aging skin in vivo", PNAS, 92(20):9363-7 (1995).
Frankel and Pabo, "Cellular uptake of the tat protein from human immunodeficiency virus", Cell, 55(6):1189-93 (1988).
Fusaki, et al., "Efficient induction of transgene-free human pluripotent stem cells using a vector based on Sendai virus, an RNA virus that does not integrate into the host genome", Proc Jpn Acad Ser., B85:348-362 (2009).
Genbank, Accession No. AAA65679.1, "immunoglobulin heavy chain, partial [Mus musculus]", 2 pages, First available May 2, 1995, accessed Mar. 28, 2016.
Genbank, Accession No., AAA65681.1, "immunoglobulin light chain, partial [Mus musculus]", 2 pages, First available May 2, 1995, accessed Mar. 28, 2016.
Genbank, Accession No. L16981.1, "Mouse Ig rearranged L-chain gene, partial cds",1 page, First available May 2, 1995, accessed Mar. 28, 2016.
Grudzien-Nogalska, et al., "Phosphorothioate cap analogs stabilize mRNA and increase translational efficiency in mammalian cells", RNA, 13(10):1745-55 (2007).
Gysin, et al., "Therapeutic strategies for targeting ras proteins", Genes Cancer, 2(3):359-72 (2011).
Hacein-Bey-Abina, et al., "LMO-2associated clonal T cell proliferation in two patients after gene therapy for SCID-X1", Science, 302(5644):415-9 (2003).
Halazonetis, et al., "An oncogene-induced DNA damage model for cancer development", Science, 319(5868):1352-5 (2008).
Hansen, et al. "antibody mediated transduction of therapeutic proteins into living cells", Scientific world, 5(9):782-8 (2005).
Harrington, et al., "VX-680, a ptent and selective small-molecule inhibitor of aurora kinases suppresses tumor growth in vivo", Nat Med., 10:262-7 (2004).
Hayflick, et al., "The limited in vitro lifetime of human diploid cell strains", Exp Cell Res., 37:614-36 (1965).
Ho, et al., "Synthetic protein transduction domains: enhanced transduction potential in vitro and in vivo", Cancer Res., 61(2):474-7 (2001).
Hoeijmakers, "DNA damage, aging, and cancer", N. Engl. J. Med. 361:1475-85 (2009).
Holtkemp, et al., "Modification of antigen-encoding RNA increases stability, translational efficacy, and T-cell stimulatory capacity of dendritic cells", Blood, 108(13):4009-17 (2006).
Hucl, et al., "A syngeneic variance library for functional annotation of human variation: application to BRCA2", Cancer Res., 68:5023-30 (2008).
Jain, et al., "Engineering antibodies for clinical applications", Trends in Biotechnol, 25(7):307-16 (2007).
Jang, et al., "Drug delivery and transport to solid tumors", Phar. Res., 20:1337-50 (2003).
Kabat, et al., "Sequences of proteins of Immunological Interest", 5 Ed Public Health service, National Institutes of Health, Bethesda Md. (1991).
Kabouridis, "Biological applications of protein transduction technology", Trends in Biotechnol., (11):498-503 (2003).
Kane, et al., "Methylation of the hMLH1 promoter correlates with lack of expression of hMLH1 in sporadic colon tumors and mismatch repair-defective human tumor cell lines", Cancer Rev., 57:808-11 (1997).
Kay, "State of the art gene-based therapies: the road ahead", Nature Rev Genetics, 12(5):316-28 (2011).
Kellner, et al., "Boosting ADCC and CDC activity by Fc engineering and evaluation of antibody effector functions", Methods, 65:105-13 (2014).
Levitt, et al., "Pten-induction in U251 glioma cells decreases the expression of insulin-like growth factor binding protein-2", Biochem Biophys Res Comm., 336:1056-61 (2005).
Lewitzky, et al., "Reprogramming somatic cells towards pluripotency by defined factors", Curr Opin Biotechnol., 18:467-73 (2007).
Li, et al., "PTEN, a putative protein tyrosine phosphatase gene mutated in human brain, breast, and prostate cancer", Science, 275:1943-7 (1997).
Liao et al "The comet assay: a sensitive method for detecting DNA damage in individual cells", Methods, 48(1):46-53 (2009).
Liu, et al., "A novel bivalent single-chain variable fragment (scFV) inhibits the action of tumor necrosis factor [alpha]", Biotechnol App Biochem., 50(4):173-9 (2008).
Maeda, et al., "Tumor vascular permeability and the EPR effect in macromolecular therapeutics: a review", J Controlled Release, 65:271-84 (2000).
McCabe, et al., "BRCA2-deficient CAPAN-1 cells are extremely sensitive to the inhibition of Poly (ADP-Ribose) polymerase: an issue of potency", Cancer Biology Therapy, 4:934-6 (2005).
McEllin, et al., "PTEN loss compromises homologous recombination repair in astrocytes: implications for glioblastoma therapy with temozolomide or poly(ADP-ribose) polymerase inhibitors", Cancer Res., 70:5457-64 (2010).
Muller, et al., "TransMabs: cell-penetrating antibodies, the next generation", Exp Opin Biol Ther., 5(2):1-5 (2005).

(56) References Cited

OTHER PUBLICATIONS

Nakanishi, et al., "Development of sendai virus vectors and their potential applications in gene therapy and regenerative medicine", Curr Gene Ther., 12 (5):410-6 (2012).
Okita, et al., "Induction of pluripotency by defined factors", Exp Cell Res., 316 (16):2565-70 (2010).
PARP Inhibitor, http://www.parp-inhibitors.com, retrieved from the internet Mar. 31, 2011.
Porter, et al., "Chimeric antigen receptor-midified T cells in chronic lymphoid leukemia", NEJM, 365(8):725-33 (2011).
Puc, et al., "PTEN loss inhibits CHK1 to cause double stranded-DNA breaks in cells", Cell Cycle, 4:927-9 (2005).
Rabinovich, et al., "Chimeric receptor mRNA transfection as a tool to generate antineoplastic lymphocytes", Human Gene Therapy, 20(1):51-61 (2009).
Rabinovich, et al., "Synthetic messenger RNA as a tool for gene therapy", Hum Gene Ther., 17(10):1027-35 (2006).
Rahman and Isenberg, "Systemic lupus erythematosus", N. Engl. J. Med. 358:929-39 (2008).
Ratnam, et al., "Current development of clinical inhibitors of poly(ADP-ribose) polymerase in oncology", Clin Cancer Res., 13(5):1383-8 (2007).
Ritter, et al., "Gene therapy in transplantation: Toward clinical trials", Curr Opin Mol Ther., 11(5):504-12 (2009).
Scott, et al., "Antibody therapy of cancer", Nature Reviews Cancer, 12:278-87 (2012).
Sliwinska, et al., "Induction of senescence with doxorubicin leads to increased genomic instability of HCT116 cells", Mech. Ageing Dev., 130:24-32 (2009).
Stanulis-Praeger, et al., "Cellular senescence revisited: a review", Mech Ageing Derv, 38:1-48 (1987).
Steck, et al., "Identification of a candidate tumour suppressor gene, MMAC1, at chromosome 10q23.3 that is mutated in multiple advanced cancers", Nat Genet., 15:356-62 (1997).
Stepinski, et al., "Synthesis and properties of mRNA\s containing the novel "anti-reverse" cap analogs 7-methyl(3\-O-methyl)GpppG and 7-methyl (3\-deoxy)GpppG", RNA 7 (10:1486-95 (2001).
te Poele, et al., "DNA damage is able to induce senescence in tumor cells in vitro and in vivo", Cancer Res. 62:1876-1883 (2002).
Vlietstra, et al., "Frequent inactivation of PTEN in prostate cancer cell lines and xenografts", Cancer Res., 58:2720-3 (1998).
Wadia and Stan, "Transducible TAT-HA fusogenic peptide enhances escape of TAT-fusion proteins after lipid raft micropinocytosis", Nat Med., 10(3):310-5 (2004).
Walpita, et al., "Reverse genetics of negative-stranded RNA viruses: a global perspective", FEMS Microbiol. Lett., 244(1):9-18 (2005).
Wang, Mutagenesis in mammalian cells induced by triple helix formation and transcription-coupled repair, Science, 271(5250):802-5 (1996).
Warren, et al., "Highly efficient reprogramming to pluripotency and directed differentiation of human cells with synthetic modified mRNA", Cell Stem Cell, 7(5):618-30 (2010).
Weisbart, et al., "An autoantibody is modified for use as a delivery system to target the cell nucleus: therapeutic implications", J Autoimmun., 11:539-46 (1998).
Weisbart, et al., "Antibody-mediated transduction of p53 selectively kills cancer cells", Int J Oncol., 25:1867-73 (2004).
Wender, et al., "The design, synthesis, and evaluation of molecules that enable or enhance cellular uptake: peptoid molecular transporters", PNAS, 97 (24):13003-8 (2000).
Yee, et al., "The fine specificity of IgG antiguanosine antibodies in systemic lupus erythematosus", Clin Immunol Immunopathol., 36(2):161-7 (1985).
Yoshizaki, et al., "Naked sendai virus vector lacking all of the envelope-related genes: reduced cytopathogenicity and immunogenicity", J Gene Med., 8 (9):1151-9 (2006).
Zack, et al., "DNA mimics a self-protein that may be a target for some anti-DNA antibodies in systemic lupus erythematosus", J. Immunol. 154(4):1987-94 (1995).

Genbank, Accession No. AAA65682.1, This CDS feature is included to show the translation of the of the corresponding V_region. Presently translation qualifiers on V_regions features are illegal, partial [Mus musculus], 1 page, First available May 2, 1995, accessed Jun. 21, 2016.
Noble, et al., "A cell-penetrating nucleoltyic lupus autoantibody damages DNA and is toxic to BRCA2-deficient cancer cells" poster presented at the Proceedings: AACR Annual Meeting 2014; Apr. 5-9, San Diego, CA (2014).
Noble, et al., "A cell-penetrating nucleolytic lupus autoantibody damages DNA and is toxic to BRCA2-deficient cancer cells", Abstract 4220, Cancer Res, 74:4220 (2014).
Noble, et al., Optimizing a lupus autoantibody for targeted cancer therapy , Cancer Res., 75(11):2285-91 (2015).
Weisbart, et al., Nuclear delivery of p53 C-terminal peptides into cancer cells using scFv fragments of a monoclonal antibody that penetrates living cells , Cancer Lttrs., 195:211-19 (2003).
Zack, et al., Novel structural features of aautoantibodies in murine lupis: A possible superantigen binding site , Immonol Cell Biol., 72:513-20 (1994).
Noble, et al., DNA-damaging autoantibodies and cancer: the lupus butterfly theory , Nature Reviews, 17:429-34 (2016).
Sancar, et al., Molecular mechanisms of mammalian NA repair and the DNA damage checkpoints , Annu Rev Biochem., 73:39-85 (2004).
Williams, DNA hydrolysis mechanism and reactivity , Nucleic Acids and Molecular Biology vol. 13, pp. 1-7, Marina Zenkova, ED Springer-Verlag Berlin Heidelberg, (2004).
Yung, et al., Anti-DNA antibodies in the pathogenesis of lupus nephritis—The emerging mechanisms , Autoimmunity Rev., 7(4):317-21 (2008).
Broson, et al., "Mutational analysis of avidity and fine specificity of anti-levan antibodies", J Immunol., 163:6694-701 (1999).
Brummel, et al., "Probing the combining site of an anti-carbohydrate antibody by saturation-mutagenesis: role of the heavy-chain CDR3 residues", Biochem., 32(4):1180-7 (1993).
Burks, et al., "In vitro scanning saturation mutagenesis of an antibody binding product", PNAS, 94:412-7 (1997).
Casset, et al., "Peptide mimetic of an anti-CD4 monoclonal antibody by rational design", BBRC, 307:198-205 (2003).
Chen, et al., "Selection and analysis of an optimized anti-VEGF antibody: Crystal structure of an affinity-matured Fab in complex with antigen", J Mol Biol., 283:865-81 (1999).
Coleman, "Effects of amino acid sequence changes on antibody-antigen interactions", Res Immunol., 145:33-6 (1994).
DePascalis, et al., "Grafting of abbreviated complementarity-determining regions containing specificity-determining residues essential for ligand contact to engineer a less immunogenic humanized monoclonal antibody", J Immun., 169:3076-84 (2002).
Ford, "Lupus antibody tops cancer cells", Sci Trans Med., 4(157):157-60 (2012).
Holm, et al., "Functional mapping and single chain construction of the anti-cytokeratin 8 monoclonal antibody TS1", Mol Immun., 44:1075-84 (2007).
Jang, et al., "The structural basis for DNA binding by an anti-DNA autoantibody", Mol Immun.,35:1207-17 (1998).
Kobayashi, et al., "Tryptophan H33 plays an important role in pyrimidine (6-4) pyrimidone photoproduct binding by a high-affinity antibody", Protein Eng., 12(10):879-84 (1999).
Kumar, et al., "Molecular cloning and expression of the fabs of human autoantibodies in *Escherichia coli*", J Bio Chem., 275:35129-36 (2000).
MacCallum, et al., "Antibody-antigen interactions: Contact analysis and binding site topography", J Mol Biol., 262:732-45 (1998).
Rudikoff, et al., "Single amino substitution altering antigen-binding specificity", PNAS, 79:1979-83 (1982).
Smith-Gill, et al., "Contributions of immunoglobulin heavy and light chains to antibody specificity for lysozyme and two haptens", J Immunol., 139:4135-44 (1987).
Song, et al., "Light chain of natural antibody plays a dominant role in protein antigen binding", Biochem Biophys Res Comm., 268:390-4 (2000).

(56) References Cited

OTHER PUBLICATIONS

Vajdos, et al., "Comprehensive functional maps of the antigen-binding site of am amti-ErbB2 antibody obtained with shotgun scanning mutagenesis", J Mol Biol., 320:415-28 (2002).

Ward, et al., "Binding activities of a repertoire of single immunoglobulin variable domains secreted from *Escherichia coli*", Nature, 341:544-6 (1989).

Wu, et al., "Humanization of a murine monoclonal antibody by simultaneous optimization of framework and CDR residues", J Mol Biol., 294:151-62 (1999).

Lee, et al., "Cell-penetrating autoantibody induces caspase-mediated apoptosis through catalytic hydrolysis of DNA," *Bioorganic & Medicinal Chemistry*, 15:2016-2023 (2007).

* cited by examiner

CELL-PENETRATING ANTI-DNA ANTIBODIES AND USES THEREOF INHIBIT DNA REPAIR

CROSS-REFERENCE TO RELATED APPLICATIONS

This application is a 371 application of the International Application No. PCT/US2012/031860, entitled "Cell-Penetrating Anti-DNA Antibodies and Uses Thereof Inhibit DNA Repair" by James E. Hansen, Peter M. Glazer, Richard H. Weisbart, Robert N. Nishimura, and Grace Chan, filed on Apr. 2, 2012, which claims benefit of and priority to U.S. Provisional Application No. 61/470,918, filed Apr. 1, 2011, which is hereby incorporated herein by reference in its entirety.

STATEMENT REGARDING FEDERALLY SPONSORED RESEARCH OR DEVELOPMENT

This invention was made with Government support under CA129186 awarded by the National Institutes of Health. The Government has certain rights in the invention. This work was supported by the U.S. Department of Veterans Affairs, and the Federal Government has certain rights in the invention.

FIELD OF THE INVENTION

The invention is generally related to the field of antibody therapy for the treatment of cancer, and more particularly to the use of cell-penetrating anti-DNA antibodies to inhibit DNA repair, sensitize cells to radiotherapy and DNA-damaging chemotherapy, and to selectively kill cancer cells with pre-existing deficiencies in DNA repair.

BACKGROUND OF THE INVENTION

Most cancer therapies are severely limited by significant side effects due to non-specific tissue toxicity, and identification of novel agents that are selectively toxic to cancer cells or selectively sensitize tumors to treatment is a key goal in cancer research. A significant amount of work has focused on applying the specific binding activity of monoclonal antibodies to the development of tumor-specific therapies. Select antibodies such as trastuzumab (Herceptin®), rituximab (Rituxan®), and cetuximab (Erbitux®) have received approval for use in human cancer therapy, but all lack the ability to penetrate into cancer cells and are therefore limited to attacking targets located on the external surface of tumor cells.

A significant number of tumor-specific targets are located inside cells and nuclei, and numerous types of cancer are particularly vulnerable to treatments that inhibit DNA repair.

It is therefore an object of the invention to provide cell-penetrating antibodies, such as anti-DNA antibodies, that inhibit DNA repair.

It is a further object of the invention to provide compositions that increase the sensitivity of cancer cells to radiation therapy and/or chemotherapy.

It is a further object of the invention to provide cell-penetrating antibodies and derivatives thereof that are selectively toxic to cancer or other undesirable cells with pre-existing deficiencies in DNA repair, typically associated with familial syndromes due to mutations in DNA repair genes but also occurring sporadically with silencing or a mutation in DNA repair genes.

It is a further object of the invention to provide cell-penetrating antibodies and derivatives thereof that prevent or inhibit viral infection, integration, and/or replication by perturbing host DNA repair.

SUMMARY OF THE INVENTION

Methods of using anti-DNA antibodies to penetrate cell nuclei and inhibit DNA repair have been developed. In preferred embodiments, the cell is a neoplasm, typically a cancer cell such as a carcinoma. The method of treating cancerous or certain infected cells involves contacting the cells with the cell-penetrating anti-DNA antibodies, alone or in combination with other agents such as chemotherapeutic agents or radiation. In some embodiments, the method involves assaying a subject or tumor for one or more gene mutations or alterations in normal gene expression that impair DNA repair, then the anti-DNA antibodies are selected for use in treating the cells if the one or more mutations or patterns of altered expression or function are identified.

Cells that have impaired DNA repair are particularly good targets for this method. In preferred embodiments, the cells are defective in the expression of or have a mutation in a gene involved in DNA repair, DNA damage checkpoints, DNA synthesis, homologous recombination, or non-homologous end-joining. Exemplary genes include XRCC1, ADPRT (PARP-1), ADPRTL2, (PARP-2), POLYMERASE BETA, CTPS, MLH1, MSH2, FANCD2, PMS2, p53, p21, PTEN, RPA, RPA1, RPA2, RPA3, XPD, ERCC1, XPF, MMS19, RAD51, RAD51b, RAD51C, RAD51D, DMC1, XRCCR, XRCC3, BRCA1, BRCA2, PALB2, RAD52, RAD54, RAD50, MRE11, NB51, WRN, BLM, KU70, KU80, ATM, ATR CHK1, CHK2, FANCA, FANCB, FANCC, FANCD1, FANCD2, FANCE, FANCF, FANCG, FANCC, FANCD1, FANCD2, FANCE, FANCF, FANCG, RAD1, and RAD9. In some embodiments, the defective gene is a tumor suppressor gene. For example, the cells can have one or more mutations in BRCA1 or BRCA2.

Many cancer therapy procedures such as chemotherapy and radiotherapy work by overwhelming the capacity of the cell to repair DNA damage, resulting in cell death. In some embodiments, the cells are resistant to radiation therapy and/or chemotherapy. Methods are also provided for enhancing the efficacy of radiotherapy and/or chemotherapy in a subject by administering to the subject a composition containing cell-penetrating anti-DNA antibodies. In some embodiments, the antibodies increase the cells' sensitivity to the radiation therapy and/or chemotherapy. The chemotherapeutics that can be enhanced by this method include those that damage DNA or inhibit DNA repair. The anti-DNA antibodies may be administered to the subject before, concurrently, or after the administration of radiotherapy and/or chemotherapy. In preferred embodiments, the anti-DNA antibodies are administered to the subject at least two days before or after radiotherapy and/or chemotherapy, more preferably at least one day before or after radiotherapy and/or chemotherapy, and even more preferably concurrently with the radiotherapy and/or chemotherapy.

Cell-penetrating anti-DNA antibodies are disclosed that inhibit DNA repair. These antibodies are transported into the nucleus of the cell without the aid of a carrier or conjugate. The anti-DNA antibody can in some embodiments bind single stranded DNA (ssDNA), double-stranded DNA (dsDNA), or a combination thereof. Antibodies specific for double-stranded DNA (dsDNA) are present in 70% of patients with systemic lupus erythematosus (SLE), compared to 0.5% of people without SLE. Therefore, in some embodiments, the cell-penetrating anti-DNA antibody is isolated or derived from a subject with SLE or an animal, such as a mouse or rabbit, with a similar autoimmune condition, then humanized or expressed recombinantly and administered as a dimer or single chain antibody.

Examples of useful cell-penetrating anti-DNA antibodies are the monoclonal anti-DNA antibody 3E10, or a variant or fragment thereof that binds the same epitope(s) as 3E10. In preferred embodiments, the anti-DNA antibody is a single chain variable fragment of an anti-DNA antibody, or conservative variant thereof. For example, the anti-DNA antibody can be a single chain variable fragment of 3E 10 (3E 10 scFv), or conservative variant thereof. The 3E10 scFv is preferably produced as a recombinant protein expressed from an expression vector in a mammalian cell, such yeast, e.g., *Pichia pastoris*.

In preferred embodiments, the antibodies have the same epitope specificity as monoclonal antibody 3E10, produced by ATCC Accession No. PTA 2439 hybridoma. This can be achieved by producing a recombinant antibody that contains the paratope of monoclonal antibody 3E10. Alternatively, this can be achieved by creating a hybridoma from lymphocytes isolated from a human subject or a mouse or other experimental animal with an autoimmune disease, such as SLE. Suitable antibodies include full-length antibodies, single chain antibodies, and antibody fragments. The antibody can also be a bispecific monoclonal antibody that specifically binds a second therapeutic target in the nucleus of the cell. For example, in some embodiments, the antibody specifically binds a protein in the nucleus of a cell such as a DNA repair protein, a DNA replication protein, a DNA damage response protein, a cell cycle regulatory protein, a DNA damage checkpoint protein, an apoptosis regulatory protein, or a stress response protein. Exemplary targets in these categories respectively include RAD52 protein, ataxia telangiectasia mutated protein (ATM), CHK2 or CHK1 proteins, BCL2 protein, heat shock protein 70 (HSP70), Myc protein, and Ras protein.

In a preferred embodiment, the cell-penetrating anti-DNA antibodies are provided in a unit dosage in an amount effective to inhibit DNA repair in a cancer, which may include a pharmaceutically acceptable excipient in the same vial or separately, in a kit, wherein the antibodies are present in an amount effective to inhibit DNA repair in a cancer cell. In preferred embodiments, the antibody is present in amount from about 200 mg/m$^2$ to about 1000 mg/m$^2$, including about 200, 250, 300, 350, 400, 450, 500, 600, 700, 800, 900, or 1000 mg/m$^2$. In some embodiments, pharmaceutical composition is in a unit dosage form for intravenous injection. In some embodiments, the pharmaceutical composition is in a unit dosage form for intratumoral injection.

The pharmaceutical composition (e.g., dosage unit) can further contain, or be provided in a kit with, additional therapeutic agents. For example, the additional therapeutic agent can be an antineoplastic agent, a radiosensitizing agent, or a combination thereof. Preferably, the antineoplastic agent damages DNA or inhibits DNA repair. In some embodiments, the antineoplastic agent is cisplatin, cytoxan, doxorubicin, methotrexate, mitomycin e, nitrogen mustard, a ribonucleotide reductase inhibitor (e.g., hydroxyurea), tirapazamine, temozolomide, or a topoisomerase inhibitor (e.g, camptothecin).

Non-limiting examples of radiosensitizers that can be present in the pharmaceutical composition include cisplatin, doxorubicin, gemcitabine, 5-fluorouracil, PARP1 inhibitors, histone deacetylase inhibitors, proteasome inhibitors, epidermal growth factor receptor (EGFR) inhibitors, insulin-like growth factor-1 (IGF-1) receptor inhibitors, CHK1 inhibitors, mTOR inhibitors, kinase inhibitors, pentoxifylline, and vinorelbine.

The pharmaceutical composition (e.g., dosage unit) can further contain one or more therapeutic monoclonal antibodies for treating cancer. In preferred embodiments, the therapeutic monoclonal antibody is bevacizumab, cetuximab, rituximab, trastuzumab, or a combination thereof.

DETAILED DESCRIPTION OF THE INVENTION

I. Definitions

Figure 1A:
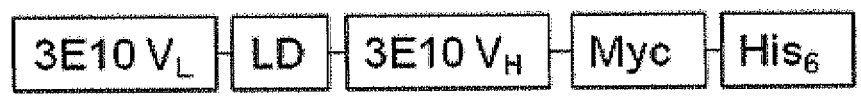
FIG. 1A is a schematic of the 3E10 single chain antibody variable fragment (3E10 scFv) composed of the variable regions of the 3E10 light and heavy chains joined by a linking domain (LD). Myc and His6 tags were added to allow for detection and purification. 3E10 scFv penetrates into the nuclei of cancer cells (demonstrated with Skov-3 ovarian cancer cells treated with 5 μM 3E10 scFv for 30 minutes, and then fixed and stained with an anti-Myc antibody).

The term "antibody" refers to natural or synthetic antibodies that selectively bind a target antigen. The term includes polyclonal and monoclonal antibodies. In addition to intact immunoglobulin molecules, also included in the term "antibodies" are fragments or polymers of those immunoglobulin molecules, and human or humanized versions of immunoglobulin molecules that selectively bind the target antigen.

The term "cell-penetrating anti-DNA antibody" refers to an antibody that is transported into the nucleus of living mammalian cells and specifically binds DNA (e.g., single-stranded and/or double-stranded DNA). In preferred embodiments, the antibody is transported into the nucleus of the cells without the aid of a carrier or conjugate. In other embodiments, the antibody is conjugated to a cell-penetrating moiety, such as a cell penetrating peptide.

The term "specifically binds" refers to the binding of an antibody to its cognate antigen (for example DNA) while not significantly binding to other antigens. Preferably, an antibody "specifically binds" to an antigen with an affinity constant (Ka) greater than about $10^5$ mol$^{-1}$ (e.g., $10^6$ mol$^{-1}$, $10^7$ mol$^{-1}$, $10^8$ mol$^{-1}$, $10^9$ mol$^{-1}$, $10^{11}$ mol$^{-1}$, and $10^{12}$ mol$^{-1}$ or more) with that second molecule.

The term "monoclonal antibody" or "MAb" refers to an antibody obtained from a substantially homogeneous population of antibodies, i.e., the individual antibodies within the population are identical except for possible naturally occurring mutations that may be present in a small subset of the antibody molecules.

The term "DNA repair" refers to a collection of processes by which a cell identifies and corrects damage to DNA molecules. Single-strand defects are repaired by base excision repair (BER), nucleotide excision repair (MER), or mismatch repair (MMR). Double-strand breaks are repaired by non-homologous end joining (NHEJ), microhomology-mediated end joining (MMEJ), or homologous recombination. After DNA damage, cell cycle checkpoints are activated, which pause the cell cycle to give the cell time to repair the damage before continuing to divide. Checkpoint mediator proteins include BRCA1, MDC1, 53BP1, p53, ATM, ATR, CHK1, CHK2, and p21.

The term "impaired DNA repair" refers to a state in which a mutated cell or a cell with altered gene expression is incapable of DNA repair or has reduced activity of one or more DNA repair pathways or takes longer to repair damage to its DNA as compared to a wild type cell.

The term "chemosensitivity" refers to the relative susceptibility of cancer cells to the effects of anticancer drugs. The more chemosensitive a cancer cell is, the less anticancer drug is required to kill that cell.

The term "radiosensitivity" refers to the relative susceptibility of cells to the harmful effect of ionizing radiation. The more radiosensitive a cell is, the less radiation that is required to kill that cell. In general, it has been found that cell radiosensitivity is directly proportional to the rate of cell division and inversely proportional to the cell's capacity for DNA repair.

The term "radioresistant" refers to a cell that does not die when exposed to clinically suitable dosages of radiation.

The term "neoplastic cell" refers to a cell undergoing abnormal cell proliferation ("neoplasia"). The growth of neoplastic cells exceeds and is not coordinated with that of the normal tissues around it. The growth typically persists in the same excessive manner even after cessation of the stimuli, and typically causes formation of a tumor.

The term "tumor" or "neoplasm" refers to an abnormal mass of tissue containing neoplastic cells. Neoplasms and tumors may be benign, premalignant, or malignant.

The term "cancer" or "malignant neoplasm" refers to a cell that displays uncontrolled growth, invasion upon adjacent tissues, and often metastasis to other locations of the body.

The term "antineoplastic" refers to a composition, such as a drug or biologic, that can inhibit or prevent cancer growth, invasion, and/or metastasis.

The term "anti-cancer moiety" refers to any agent, such as a peptide, protein, nucleic acid, or small molecule, which can be combined with the disclosed anti-DNA antibodies to enhance the anti-cancer properties of the antibodies. The term includes antineoplastic drugs, antibodies that bind and inhibit other therapeutic targets in cancer cells, and substances having an affinity for cancer cells for directed targeting of cancer cells.

The term "virally transformed cell" refers to a cell that has been infected with a virus or that has incorporated viral DNA or RNA into its genome. The virus can be an acutely-transforming or slowly-transforming oncogenic virus. In acutely transforming viruses, the viral particles carry a gene that encodes for an overactive oncogene called viral-oncogene (v-one), and the infected cell is transformed as soon as v-one is expressed. In contrast, in slowly-transforming viruses, the virus genome is inserted near a proto-oncogene in the host genome. Exemplary oncoviruses include Human papillomaviruses (HPV), Hepatitis B (HBV), Hepatitis C(HCV), Human T-lymphotropic virus (HTLV), Kaposi's sarcoma-associated herpesvirus (HHV-8), Merkel cell polyomavirus, Epstein-Barr virus (EBV), Human immunodeficiency virus (HIV), and Human cytomegalovirus (CMV).

A virally infected cell refers to a cell that has been exposed to or infected with a virus or carries viral genetic material, either RNA or DNA. The virus can be an oncogenic virus or a lytic virus or a latent virus and can cause cancer, immunodeficiency, hepatitis, encephalitis, pneumonitis, respiratory illness, or other disease condition. it has previously been shown that retorviruses, specifically HIV, rely in part upon the base excision repair (BER) pathway for integration into host DNA. The ability of 3E10 to inhibit DNA repair provides a mechanism whereby 3E10 and other anti-DNA antibodies can ameliorate virally caused diseases, in particular, by interfering with DNA repair and thereby by blocking the DNA or RNA metabolism that is part of virus life cycles as well as part of viral infection of a cell. The examples demonstrate that 3E10 inhibits the BER pathway, supporting efficacy in suppressing infectivity of such retroviruses.

The term "individual," "host," "subject," and "patient" are used interchangeably to refer to any individual who is the target of administration or treatment. The subject can be a vertebrate, for example, a mammal. Thus, the subject can be a human or veterinary patient.

The term "therapeutically effective" means that the amount of the composition used is of sufficient quantity to ameliorate one or more causes or symptoms of a disease or disorder. Such amelioration only requires a reduction or alteration, not necessarily elimination. A therapeutically effective amount of a composition for treating cancer is preferably an amount sufficient to cause tumor regression or to sensitize a tumor to radiation or chemotherapy.

The term "pharmaceutically acceptable" refers to a material that is not biologically or otherwise undesirable, i.e., the material may be administered to a subject without causing any undesirable biological effects or interacting in a deleterious manner with any of the other components of the pharmaceutical composition in which it is contained. The carrier would naturally be selected to minimize any degradation of the active ingredient and to minimize any adverse side effects in the subject, as would be well known to one of skill in the art.

The term "treatment" refers to the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder.

The term "inhibit" means to decrease an activity, response, condition, disease, or other biological parameter. This can include, but is not limited to, the complete ablation of the activity, response, condition, or disease. This may also include, for example, a 10% reduction in the activity, response, condition, or disease as compared to the native or control level. Thus, the reduction can be a 10, 20, 30, 40, 50, 60, 70, 80, 90, 100%, or any amount of reduction in between as compared to native or control levels.

A "fusion protein" refers to a polypeptide formed by the joining of two or more polypeptides through a peptide bond formed between the amino terminus of one polypeptide and the carboxyl terminus of another polypeptide. The fusion protein can be formed by the chemical coupling of the constituent polypeptides or it can be expressed as a single polypeptide from a nucleic acid sequence encoding the single contiguous fusion protein. A single chain fusion protein is a fusion protein having a single contiguous polypeptide backbone. Fusion proteins can be prepared using conventional techniques in molecular biology to join the two genes in frame into a single nucleic acid sequence, and then expressing the nucleic acid in an appropriate host cell under conditions in which the fusion protein is produced.

II. Compositions

A. Anti-DNA Antibodies

Cell penetrating anti-DNA antibodies are disclosed for use in enhancing sensitivity of targeted cells to chemotherapy and/or radiation. Autoantibodies to single or double stranded deoxyribonucleic acid (DNA) are frequently identified in the serum of patients with systemic lupus erythematosus (SLE) and are often implicated in disease pathogenesis. Therefore, in some embodiments, anti-DNA antibodies can be derived or isolated from patients with SLE. In preferred embodiments, the anti-DNA antibodies are monoclonal antibodies, or fragments or variants thereof. The presence of circulating autoantibodies reactive against DNA (anti-DNA antibodies) is a hallmark laboratory finding in patients with systemic lupus erythematosus (SLE). Although the precise role of anti-DNA antibodies in SLE is unclear, it has been suggested that the antibodies play an active role in SLE pathophysiology. In the early 1990s a murine lupus anti-DNA antibody, 3E10, was tested in experimental vaccine therapy for SLE. These efforts were aimed at developing anti-idiotype antibodies that would specifically bind anti-DNA antibody in SLE patients. However, 3E10 was serendipitously found to penetrate into living cells and nuclei without causing any observed cytotoxicity (Weisbart R H, et al. *J Immunol*. 1990 144(7): 2653-2658; Zack D J, et al. *J Immunol*. 1996 157(5): 2082-2088). Studies on 3E10 in SLE vaccine therapy were then supplanted by efforts focused on development of 3E10 as a molecular delivery vehicle for transport of therapeutic molecules into cells and nuclei. Other antibodies were also reported to penetrate cells.

The 3E10 antibody and its single chain variable fragment (3E10 scFv) penetrate into cells and nuclei and have proven capable of transporting therapeutic protein cargoes attached to the antibody either through chemical conjugation or recombinant fusion. Protein cargoes delivered to cells by 3E10 or 3E10 scFv include catalase, p53, and Hsp70 (Weisbart R H, et al. *J Immunol*. 2000 164: 6020-6026; Hansen J E, et al. *Cancer Res*. 2007 Feb. 15; 67(4): 1769-74; Hansen J E, et al. *Brain Res*. 2006 May 9; 1088(1): 187-96). 3E10 scFv effectively mediated delivery of Hsp70 to neurons in vivo and this resulted in decreased cerebral infarct volumes and improved neurologic function in a rat stroke model (Zhan X, et al. *Stroke*. 2010 41(3): 538-43).

It has now been discovered that 3E10 and 3E10 scFv, without being conjugated to any therapeutic protein, enhance cancer cell radiosensitivity and chemosensitivity and that this effect is potentiated in cells deficient in DNA repair. Moreover, 3E10 and 3E10 scFv are selectively lethal to cancer cells deficient in DNA repair even in the absence of radiation or chemotherapy. The Food and Drug Administration (FDA) has established a pathway for the development of monoclonal antibodies into human therapies, and 3E10 has already been approved by the FDA for use in a Phase I human clinical trial designed to test the efficacy of 3E10 in experimental vaccine therapy for SLE (Spertini F, et al. *J Rheumatol*. 1999 26(12): 2602-8). Therefore, these types of antibodies can be used for targeted therapy for cancers deficient in DNA repair as well as in new targeted therapies for cancer to potentiate other cancer treatment modalities in cancers proficient in DNA repair as well as in cancers deficient in DNA repair.

Other cell-penetrating antibodies are known, both naturally occurring in SLE patients, and obtained by screening of antibody libraries or derivatization of known cell penetrating antibodies. In some embodiments, anti-DNA antibodies are conjugated to a cell-penetrating moiety, such as a cell penetrating peptide, to facilitate entry into the cell and transport to the nucleus. Examples of cell-penetrating peptides include, but are not limited to, Polyarginine (e.g., $R_9$), Antennapedia sequences, TAT, HIV-Tat, Penetratin, Antp-3A (Antp mutant), Buforin II, Transportan, MAP (model amphipathic peptide), K-FGF, Ku70, Prion, pVEC, Pep-1, SynB1, Pep-7, HN-1, BGSC (Bis-Guanidinium-Spermidine-Cholesterol, and BGTC (Bis-Guanidinium-Tren-Cholesterol). In other embodiments, the antibody is modified using TransMabs™ technology (InNexus Biotech., Inc., Vancouver, BC).

In preferred embodiments, the anti-DNA antibody is transported into the nucleus of the cells without the aid of a carrier or conjugate. For example, the monoclonal antibody 3E10 and active fragments thereof that are transported in vivo to the nucleus of mammalian cells without cytotoxic effect are disclosed in U.S. Pat. Nos. 4,812,397 and 7,189,396 to Richard Weisbart, describing 3E10 antibodies and methods of producing and modifying 3E10 antibodies. Briefly, the antibodies may be prepared by fusing spleen cells from a host having elevated serum levels of anti-DNA antibodies (e.g., MRL/1pr mice) with myeloma cells in accordance with known techniques or by transforming the spleen cells with an appropriate transforming vector to immortalize the cells. The cells may be cultured in a selective medium and screened to select antibodies that bind DNA.

Antibodies that can be used include whole immunoglobulin (i.e., an intact antibody) of any class, fragments thereof, and synthetic proteins containing at least the antigen binding variable domain of an antibody. The variable domains differ in sequence among antibodies and are used in the binding and specificity of each particular antibody for its particular antigen. However, the variability is not usually evenly distributed through the variable domains of antibodies. It is typically concentrated in three segments called complementarity determining regions (CDRs) or hypervariable regions both in the light chain and the heavy chain variable domains. The more highly conserved portions of the variable domains are called the framework (FR). The variable domains of native heavy and light chains each comprise four FR regions, largely adopting a beta-sheet configuration, connected by three CDRs, which form loops connecting, and in some cases forming part of, the beta-sheet structure. The CDRs in each chain are held together in close proximity by the FR regions and, with the CDRs from the other chain, contribute to the formation of the antigen binding site of antibodies. Therefore, the antibodies contain at least the components of the CDRs necessary to penetrate cells, maintain DNA binding and/or interfere with DNA repair. The variable region of 3E10 contains all three properties.

Also disclosed are fragments of antibodies which have bioactivity. The fragments, whether attached to other sequences or not, include insertions, deletions, substitutions, or other selected modifications of particular regions or specific amino acids residues, provided the activity of the fragment is not significantly altered or impaired compared to the non-modified antibody or antibody fragment.

Techniques can also be adapted for the production of single-chain antibodies specific to an antigenic protein. Methods for the production of single-chain antibodies are well known to those of skill in the art. A single chain antibody can be created by fusing together the variable domains of the heavy and light chains using a short peptide linker, thereby reconstituting an antigen binding site on a single molecule. Single-chain antibody variable fragments (scFvs) in which the C-terminus of one variable domain is tethered to the N-terminus of the other variable domain via a 15 to 25 amino acid peptide or linker have been developed without significantly disrupting antigen binding or specificity of the binding. The linker is chosen to permit the heavy chain and light chain to bind together in their proper conformational orientation.

The anti-DNA antibodies can be modified to improve their therapeutic potential. For example, in some embodiments, the cell-penetrating anti-DNA antibody is conjugated to another antibody specific for a second therapeutic target in the nucleus of the cancer cell. For example, the cell-penetrating anti-DNA antibody can be a fusion protein containing 3E10 scFv and a single chain variable fragment of a monoclonal antibody that specifically binds the second therapeutic target. In other embodiments, the cell-penetrating anti-DNA antibody is a bispecific antibody having a first heavy chain and a first light chain from 3E10 and a second heavy chain and a second light chain from a monoclonal antibody that specifically binds the second therapeutic target.

Divalent single-chain variable fragments (di-scFvs) can be engineered by linking two scFvs. This can be done by producing a single peptide chain with two VH and two VL regions, yielding tandem scFvs. ScFvs can also be designed with linker peptides that are too short for the two variable regions to fold together (about five amino acids), forcing scFvs to dimerize. This type is known as diabodies. Diabodies have been shown to have dissociation constants up to 40-fold lower than corresponding scFvs, meaning that they have a much higher affinity to their target. Still shorter linkers (one or two amino acids) lead to the formation of trimers (triabodies or tribodies). Tetrabodies have also been produced. They exhibit an even higher affinity to their targets than diabodies.

The therapeutic function of the antibody can be enhanced by coupling the antibody or a fragment thereof with a therapeutic agent. Such coupling of the antibody or fragment with the therapeutic agent can be achieved by making an immunoconjugate or by making a fusion protein, or by linking the antibody or fragment to a nucleic acid such as an siRNA or to a small molecule, comprising the antibody or antibody fragment and the therapeutic agent.

A recombinant fusion protein is a protein created through genetic engineering of a fusion gene. This typically involves removing the stop codon from a cDNA sequence coding for the first protein, then appending the cDNA sequence of the second protein in frame through ligation or overlap extension PCR. The DNA sequence will then be expressed by a cell as a single protein. The protein can be engineered to include the full sequence of both original proteins, or only a portion of either. If the two entities are proteins, often linker (or "spacer") peptides are also added which make it more likely that the proteins fold independently and behave as expected.

Methods for humanizing non-human antibodies are well known in the art. Generally, a humanized antibody has one or more amino acid residues introduced into it from a source that is non-human. These non-human amino acid residues are often referred to as "import" residues, which are typically taken from an "import" variable domain. Antibody humanization techniques generally involve the use of recombinant DNA technology to manipulate the DNA sequence encoding one or more polypeptide chains of an antibody molecule.

In some embodiments, the cell-penetrating antibody is modified to alter its half-life. In some embodiments, it is desirable to increase the half-life of the antibody so that it is present in the circulation or at the site of treatment for longer periods of time. For example, where the anti-DNA antibodies are being used alone to treat cancer, e.g., cancer cells having impaired DNA repair, it may be desirable to maintain titers of the antibody in the circulation or in the location to be treated for extended periods of time. In other embodiments, the half-life of the anti-DNA antibody is decreased to reduce potential side effects. For example, where the antibody is being used in conjunction with radiotherapy or chemotherapy, the antibody is preferably present in the circulation at high doses during the treatment with radiation or antineoplastic drug but is otherwise quickly removed from the circulation. Antibody fragments, such as 3E 10 scFv, are expected to have a shorter half-life than full size antibodies. Other methods of altering half-life are known and can be used in the described methods. For example, antibodies can be engineered with Fc variants that extend half-life, e.g., using Xtend™ antibody half-life prolongation technology (Xencor, Monrovia, Calif.).

B. Cancers and Virally Transformed Cells

The antibodies can be used to treat cells undergoing unregulated growth, invasion, or metastasis. Cancer cells that have impaired DNA repair are particularly good targets for cell-penetrating anti-DNA antibodies. In some embodiments, the cell-penetrating anti-DNA antibodies are lethal to cells with impaired DNA repair. In preferred embodiments, the cells are defective in the expression of a gene involved in DNA repair, DNA synthesis, or homologous recombination. Exemplary genes include XRCC1, ADPRT (PARP-1), ADPRTL2, (PARP-2), POLYMERASE BETA, CTPS, MLH1, MSH2, FANCD2, PMS2, p53, p21, PTEN, RPA, RPA1, RPA2, RPA3, XPD, ERCC1, XPF, MMS19, RAD51, RAD51B, RAD51C, RAD51D, DMC1, XRCCR, XRCC3, BRCA1, BRCA2, PALB2, RAD52, RAD54, RAD50, MRE11, NB51, WRN, BLM, KU70, KU80, ATM, ATR CHK1, CHK2, FANCA, FANCB, FANCC, FANCD1, FANCD2, FANCE, FANCF, FANCG, FANCC, FANCD1, FANCD2, FANCE, FANCF, FANCG, RAD1, and RAD9. In some embodiments, the defective gene is a tumor suppressor gene. In preferred embodiments, the cells have one or more mutations in BRCA1 or BRCA2. Gene mutations, such as BRCA1 and BRCA2 mutations, can be identified using standard PCR, hybridization, or sequencing techniques.

Therefore, in some embodiments, the anti-DNA antibodies can be used to treat cancers arising from DNA repair deficient familial syndromes, such as breast, ovarian, and pancreatic cancers. In these embodiments, the anti-DNA antibodies can be effective without radiotherapy or chemotherapy. For example, the anti-DNA antibodies can be used to treat cancers that are linked to mutations in BRCA1, BRCA2, PALB2, OR RAD51B, RAD51C, RAD51D or related genes. The anti-DNA antibodies can also be used to treat colon cancers, endometrial tumors, or brain tumors linked to mutations in genes associated with DNA mismatch repair, such as MSH2, MLH1, PMS2, and related genes. The anti-DNA antibodies can also be used to treat cancers with silenced DNA repair genes, such as BRCA1, MLH1, OR RAD51B, RAD51C, OR RAD51D. In these preferred embodiments, the ability of the anti-DNA antibodies to inhibit DNA repair combined with the inherent repair deficiencies of these cancers can be sufficient to induce cell death.

Therefore, in some embodiments, the anti-DNA antibodies can be used to treat virally transformed cells, such as cells infected with an oncovirus. Viral transformation can impose phenotypic changes on cell, such as high saturation density, anchorage-independent growth, loss of contact inhibition, loss of orientated growth, immortalization, and disruption of the cell's cytoskeleton. The persistence of at least part of the viral genome within the cell is required for cell transformation. This may be accompanied by the continual expression from a number of viral genes, such as oncogenes. These genes may interfere with a cell's signaling pathway causing the observed phenotypic changes of the cell. In some cases, the viral genome is inserted near a proto-oncogene in the host genome. The end result is a transformed cell showing increased cell division, which is favorable to the virus. In some embodiments, viral transformation, viral infection, and/or metabolism is dependent upon DNA repair mechanisms. In these embodiments, inhibition of DNA repair using the disclosed anti-DNA antibodies also inhibits viral transformation, viral infection and/or metabolism in the cell.

In some embodiments, viral transformation, viral infection, and/or metabolism is dependent upon metabolism of the virally encoded RNA or DNA as a part of the virus life cycle, producing intermediates subject to binding and/or inhibition by 3E10 or other anti-DNA antibodies. In these embodiments, treatment with the disclosed anti-DNA antibodies also inhibits viral transformation, viral infection and/or metabolism in the cell.

Lentiviruses (such as HIV) have been previously found to be dependent on host BER activity for infection and integration (Yoder et al., *PLoS One*, 2011 Mar. 6(3) e17862). In addition, the ataxia-telangiectesia-mutated (ATM) DNA-damage response appears to be critical to HIV replication (Lau et al., *Nat Cell Biol*, 2005 7(5): 493-500). In some embodiments, retroviral (including lentiviruses, HIV) infection and integration is dependent on host DNA repair mechanisms. In these embodiments treatment with the disclosed anti-DNA antibodies also suppresses viral infection/integration and suppresses re-infection in the viral life cycle.

In some embodiments, lentiviral (HIV) replication is dependent on DNA repair. In these embodiments treatment with the disclosed anti-DNA antibodies also suppresses viral replication and suppresses re-infection in the viral life cycle. Therefore, anti-DNA antibodies can be used to treat cells infected with a virus, such as an oncovirus. In some embodiments, antibodies inhibit viral transformation, replication, metabolism, or a combination thereof. Exemplary oncoviruses that can be affected by anti-DNA antibodies include Human papillomaviruses (HPV), Hepatitis B (HBV), Hepatitis C (HCV), Human T-lymphotropic virus (HTLV), Kaposi's sarcoma-associated herpesvirus (HHV-8), Merkel cell polyomavirus, Epstein-Barr virus (EBV), Human immunodeficiency virus (HIV), and Human cytomegalovirus (CMV). Anti-DNA antibodies may also be used to treat a latent virus. In some embodiments, the failure of infected cells to mount a DNA damage response to viruses, such as HSV-1, contribute to the establishment of latency. These virally infected cells therefore have impaired DNA repair and are susceptible to treatment with anti-DNA antibodies. Exemplary latent viruses include CMV, EBV, Herpes simplex virus (type 1 and 2), and Varicella zoster virus.

Anti-DNA antibodies may also be used to treat active viral infections due to viruses that give rise to cancer, immunodeficiency, hepatitis, encephalitis, pneumonitis, respiratory illness, or other disease condition, by virtue of the antibodies' ability to bind to DNA and to interfere with DNA repair or RNA metabolisms that is part of the virus life cycle.

Representative viruses whose life cycle or symptoms of the resulting infection, that may be affected by administration of the antibodies include Human papillomaviruses (HPV), Hepatitis B (HBV), Hepatitis C(HCV), Human T-lymphotropic virus (HTLV), Kaposi's sarcoma-associated herpesvirus (HHV-8), Merkel cell polyomavirus, Epstein-Barr virus (EBV), Human immunodeficiency virus (HIV), and Human cytomegalovirus (CMV).

Additional viruses that may be affected by administration of the antibodies include parvovirus, poxvirus, herpes virus, and other DNA viruses:

| Virus Family | Examples (common names) | Virion naked/ enveloped | Capsid Symmetry | Nucleic acid type | Group |
|---|---|---|---|---|---|
| 1. Adenoviridae | Adenovirus, Infectious canine hepatitis virus | Naked | Icosahedral | ds | I |
| 2. Papillomaviridae | Papillomavirus | Naked | Icosahedral | ds circular | I |
| 3. Parvoviridae | Parvovirus B19, Canine parvovirus | Naked | Icosahedral | ss | II |
| 4. Herpesviridae | Herpes simplex virus, varicella-zoster virus, cytomegalovirus, Epstein-Barr virus | Enveloped | Icosahedral | ds | I |
| 5. Poxviridae | Smallpox virus, cow pox virus, sheep pox virus, orf virus, monkey pox virus, vaccinia virus | Complex coats | Complex | ds | I |
| 6. Hepadnaviridae | Hepatitis B virus | Enveloped | Icosahedral | circular, partially ds | VII |
| 7. Polyomaviridae | Polyoma virus; JC virus (progressive multifocal leukoencephalopathy) | Naked | Icosahedral | ds circular | I |
| 8. Anelloviridae | Torque teno virus | | | | |

RNA viruses that may be affected by administration of the antibodies include:

| Virus Family | Examples (common names) | Capsid naked/enveloped | Capsid Symmetry | Nucleic acid type | Group |
|---|---|---|---|---|---|
| 1. Reoviridae | Reovirus, Rotavirus | Naked | Icosahedral | ds | III |
| 2. Picornaviridae | Enterovirus, Rhinovirus, Hepatovirus, Cardiovirus, Aphthovirus, Poliovirus, Parechovirus, Erbovirus, Kobuvirus, Teschovirus, Coxsackie | Naked | Icosahedral | ss | IV |
| 3. Caliciviridae | Norwalk virus | Naked | Icosahedral | ss | IV |
| 4. Togaviridae | Rubella virus | Enveloped | Icosahedral | ss | IV |

-continued

| Virus Family | Examples (common names) | Capsid naked/enveloped | Capsid Symmetry | Nucleic acid type | Group |
|---|---|---|---|---|---|
| 5. Arenaviridae | Lymphocytic choriomeningitis virus | Enveloped | Complex | ss(—) | V |
| 6. Flaviviridae | Dengue virus, Hepatitis C virus, Yellow fever virus | Enveloped | Icosahedral | ss | IV |
| 7. Orthomyxoviridae | Influenzavirus A, Influenzavirus B, Influenzavirus C, Isavirus, Thogotovirus | Enveloped | Helical | ss(—) | V |
| 8. Paramyxoviridae | Measles virus, Mumps virus, Respiratory syncytial virus, Rinderpest virus, Canine distemper virus | Enveloped | Helical | ss(—) | V |
| 9. Bunyaviridae | California encephalitis virus, Hantavirus | Enveloped | Helical | ss(—) | V |
| 10. Rhabdoviridae | Rabies virus | Enveloped | Helical | ss(—) | V |
| 11. Filoviridae | Ebola virus, Marburg virus | Enveloped | Helical | ss(—) | V |
| 12. Coronaviridae | Corona virus | Enveloped | Helical | ss | IV |
| 13. Astroviridae | Astrovirus | Naked | Icosahedral | ss | IV |
| 14. Bornaviridae | Borna disease virus | Enveloped | Helical | ss(—) | V |
| 15. Arteriviridae | Arterivirus, Equine Arteritis Virus | Enveloped | Icosahedral | ss | IV |
| 16. Hepeviridae | Hepatitis E virus | Naked | Icosahedral | ss | IV |

Retroviruses may also be affected:

Genus *Alpharetrovirus*; type species: Avian leukosis virus; others include *Rous sarcoma* virus Genus *Betaretrovirus*; type species: Mouse mammary tumour virus Genus *Gammaretrovirus*; type species: Murine leukemia virus; others include Feline leukemia virus Genus *Deltaretrovirus*; type species: Bovine leukemia virus; others include the cancer-causing Human T-lymphotropic virus Genus *Epsilonretrovirus*; type species: Walleye dermal sarcoma virus Genus *Lentivirus*; type species: Human immunodeficiency virus 1; others include Simian, Feline immunodeficiency viruses Genus *Spumavirus*; type species: Simian foamy virus Family Hepadnaviridae—e.g. Hepatitis B virus Other viral diseases that may be affected by administration of the antibodies include Colorado Tick Fever (caused by Coltivirus, RNA virus), West Nile Fever (encephalitis, caused by a flavivirus that primarily occurs in the Middle East and Africa), Yellow Fever, Rabies (caused by a number of different strains of neurotropic viruses of the family Rhabdoviridae), viral hepatitis, gastroenteritis (viral)-acute viral gastroenteritis caused by Norwalk and Norwalk-like viruses, rotaviruses, caliciviruses, and astroviruses, poliomyelitis, influenza (flu), caused by orthomyxoviruses that can undergo frequent antigenic variation, measles (rubeola), paramyxoviridae, mumps, Respiratory syndromes including viral pneumonia and acute respiratory syndromes including croup caused by a variety of viruses collectively referred to as acute respiratory viruses, and respiratory illness caused by the respiratory syncytial virus (RSV, the most dangerous cause of respiratory infection in young children).

In some embodiments, the anti-DNA antibodies can be used in combination with radiotherapy, chemotherapy, or a combination thereof, to treat any cancer, including carcinomas, gliomas, sarcomas, or lymphomas. In these embodiments, the anti-DNA antibodies can sensitize the cells to the DNA-damaging effects of radiotherapy or chemotherapy. A representative but non-limiting list of cancers that the antibodies can be used to treat include cancers of the blood and lymphatic system (including leukemias, Hodgkin's lymphomas, non-Hodgkin's lymphomas, solitary plasmacytoma, multiple myeloma), cancers of the genitourinary system (including prostate cancer, bladder cancer, renal cancer, urethral cancer, penile cancer, testicular cancer), cancers of the nervous system (including mengiomas, gliomas, glioblastomas, ependymomas) cancers of the head and neck (including squamous cell carcinomas of the oral cavity, nasal cavity, nasopharyngeal cavity, oropharyngeal cavity, larynx, and paranasal sinuses), lung cancers (including small cell and non-small cell lung cancer), gynecologic cancers (including cervical cancer, endometrial cancer, vaginal cancer, vulvar cancer ovarian and fallopian tube cancer), gastrointestinal cancers (including gastric, small bowel, colorectal, liver, hepatobiliary, and pancreatic cancers), skin cancers (including melanoma, squamous cell carcinomas, and basal cell carcinomas), breast cancer (including ductal and lobular cancer), and pediatric cancers (including neuroblastoma, Ewing's sarcoma, Wilms tumor, medulloblastoma).

In some embodiments, the cancer is a neoplasm or tumor that demonstrates some resistance to radiotherapy or chemotherapy. Cancers that are resistant to radiotherapy using standard methods include, but are not limited to, sarcomas, renal cell cancer, melanoma, lymphomas, leukemias, carcinomas, blastomas, and germ cell tumors.

C. Radiotherapy

The disclosed cell-penetrating anti-DNA antibodies can be used in combination with radiation therapy, Radiation therapy (a.k.a. radiotherapy) is the medical use of ionizing radiation as part of cancer treatment to control malignant cells. Radiotherapy also has several applications in non-malignant conditions, such as the treatment of trigeminal neuralgia, severe thyroid eye disease, pterygium, pigmented villonodular synovitis, prevention of keloid scar growth, and prevention of heterotopic ossification. In some embodiments, anti-DNA antibodies are used to increase radiosensitivity for a non-malignant condition.

Radiation therapy works by damaging the DNA of dividing cells, e.g., cancer cells. This DNA damage is caused by one of two types of energy, photon or charged particle. This damage is either direct or indirect. Indirect ionization happens as a result of the ionization of water, forming free radicals, notably hydroxyl radicals, which then damage the DNA. For example, most of the radiation effect caused by photon therapy is through free radicals. One of the major limitations of photon radiotherapy is that the cells of solid tumors become deficient in oxygen, and tumor cells in a hypoxic environment may be as much as 2 to 3 times more resistant to radiation damage than those in a normal oxygen environment.

Direct damage to cancer cell DNA occurs through high-LET (linear energy transfer) charged particles such as proton, boron, carbon or neon ions. This damage is independent of tumor oxygen supply because these particles act mostly via direct energy transfer usually causing double-stranded DNA breaks. Due to their relatively large mass, protons and other charged particles have little lateral side scatter in the tissue; the beam does not broaden much, stays focused on the tumor shape and delivers small dose side-effects to surrounding tissue. The amount of radiation used in photon radiation therapy is measured in Gray (Gy), and varies depending on the type and stage of cancer being treated. For curative cases, the typical dose for a solid epithelial tumor ranges from 60 to 80 Gy, while lymphomas are treated with 20 to 40 Gy. Post-operative (adjuvant) doses are typically around 45-60 Gy in 1.8-2 Gy fractions (for breast, head, and neck cancers). Many other factors are considered by radiation oncologists when selecting a dose, including whether the patient is receiving chemotherapy, patient co-morbidities, whether radiation therapy is being administered before or after surgery, and the degree of success of surgery.

The response of a cancer to radiation is described by its radiosensitivity. Highly radiosensitive cancer cells are rapidly killed by modest doses of radiation. These include leukemias, most lymphomas and germ cell tumors. The majority of epithelial cancers are only moderately radiosensitive, and require a significantly higher dose of radiation (60-70 Gy) to achieve a radical cure. Some types of cancer are notably radioresistant, that is, much higher doses are required to produce a radical cure than may be safe in clinical practice. Renal cell cancer and melanoma are generally considered to be radioresistant.

The response of a tumor to radiotherapy is also related to its size. For complex reasons, very large tumors respond less well to radiation than smaller tumors or microscopic disease. Various strategies are used to overcome this effect. The most common technique is surgical resection prior to radiotherapy. This is most commonly seen in the treatment of breast cancer with wide local excision or mastectomy followed by adjuvant radiotherapy. Another method is to shrink the tumor with neoadjuvant chemotherapy prior to radical radiotherapy. A third technique is to enhance the radiosensitivity of the cancer by giving certain drugs during a course of radiotherapy. The disclosed cell-penetrating anti-DNA antibodies serve this third function. In these embodiments, the anti-DNA antibody increases the cell's sensitivity to the radiotherapy, for example, by at least 10%, 15%, 20%, 25%, 30%, 35%, 40%, 45%, 50%. Moreover, the cell penetrating anti-DNA antibodies can be combined with one or more additional radiosensitizers. Examples of known radiosensitizers include cisplatin, gemcitabine, 5-fluorouracil, pentoxifylline, vinorelbine, PARP inhibitors, histone deacetylase inhibitors, and proteasome inhibitors.

D. Chemotherapeutics

Numerous chemotherapeutics, especially antineoplastic drugs, are available for combination with the antibodies. The majority of chemotherapeutic drugs can be divided into alkylating agents, antimetabolites, anthracyclines, plant alkaloids, topoisomerase inhibitors, monoclonal antibodies, and other antitumour agents.

In preferred embodiments, the antineoplastic drug damages DNA or interferes with DNA repair since these activities will synergize most effectively with the anti-DNA antibody. In these embodiments, the antibody increases the cell's sensitivity to the chemotherapy, for example, by at least 10%, 15%, 20%, 25%, 30%, 35%, 40%, 45%, 50%. Non-limiting examples of antineoplastic drugs that damage DNA or inhibit DNA repair include carboplatin, carmustine, chlorambucil, cisplatin, cyclophosphamide, dacarbazine, daunorubicin, doxorubicin, epirubicin, idarubicin, ifosfamide, lomustine, mechlorethamine, mitoxantrone, oxaliplatin, procarbazine, temozolomide, and valrubicin. In some embodiments, the antineoplastic drug is temozolomide, which is a DNA damaging alkylating agent commonly used against glioblastomas. In some embodiments, the antineoplastic drug is a PARP inhibitor, which inhibits a step in base excision repair of DNA damage. In some embodiments, the antineoplastic drug is a histone deacetylase inhibitor, which suppresses DNA repair at the transcriptional level and disrupt chromatin structure. In some embodiments, the antineoplastic drug is a proteasome inhibitor, which suppresses DNA repair by disruption of ubiquitin metabolism in the cell. Ubiquitin is a signaling molecule that regulates DNA repair. In some embodiments, the antineoplastic drug is a kinase inhibitor, which suppresses DNA repair by altering DNA damage response signaling pathways.

In other embodiments, the antineoplastic drug complements the anti-DNA antibodies by targeting a different activity in the cancer cell. In these embodiments, the antineoplastic drug does not inhibit DNA repair or damage DNA.

Examples of antineoplastic drugs that can be combined with the cell-penetrating anti-DNA antibodies include, but are not limited to, alkylating agents (such as temozolomide, cisplatin, carboplatin, oxaliplatin, mechlorethamine, cyclophosphamide, chlorambucil, dacarbazine, lomustine, carmustine, procarbazine, chlorambucil and ifosfamide), antimetabolites (such as fluorouracil, gemcitabine, methotrexate, cytosine arabinoside, fludarabine, and floxuridine), some antimitotics, and vinca alkaloids such as vincristine, vinblastine, vinorelbine, and vindesine), anthracyclines (including doxorubicin, daunorubicin, valrubicin, idarubicin, and epirubicin, as well as actinomycins such as actinomycin D), cytotoxic antibiotics (including mitomycin, plicamycin, and bleomycin), and topoisomerase inhibitors (including camptothecins such as irinotecan and topotecan and derivatives of epipodophyllotoxins such as amsacrine, etoposide, etoposide phosphate, and teniposide).

E. Pharmaceutical Compositions

The cell-penetrating anti-DNA antibodies can be used therapeutically in combination with a pharmaceutically acceptable carrier. In some embodiments, the pharmaceutical composition is a unit dosage containing a cell-penetrating anti-DNA antibody or fragment thereof in a pharmaceutically acceptable excipient, wherein the antibody is present in an amount effective to inhibit DNA repair in a cancer or infected cell. In preferred embodiments, the antibody is present in amount from about 200 mg/m$^2$ to about 1000 mg/m$^2$, more preferably about 200, 250, 300, 350, 400, 450, 500, 600, 700, 800, 900, or 1000 mg/m$^2$. In some embodiments, the unit dosage is in a unit dosage form for intravenous injection. In some embodiments, the unit dosage is in a unit dosage form for intratumoral injection.

The materials may be in solution, emulsions, or suspension (for example, incorporated into microparticles, liposomes, or cells). Typically, an appropriate amount of a pharmaceutically-acceptable salt is used in the formulation to render the formulation isotonic. Examples of pharmaceutically-acceptable carriers include, but are not limited to, saline, Ringer's solution and dextrose solution. The pH of the solution is preferably from about 5 to about 8, and more preferably from about 7 to about 7.5. Pharmaceutical compositions may include carriers, thickeners, diluents, buffers, preservatives, and surface active agents. Further carriers include sustained release preparations such as semi-permeable matrices of solid hydrophobic polymers containing the antibody, which matrices are in the form of shaped particles, e.g., films, liposomes or microparticles. It will be apparent to those persons skilled in the art that certain carriers may be more preferable depending upon, for instance, the route of administration and concentration of composition being administered. Pharmaceutical compositions may also include one or more active ingredients such as antimicrobial agents, anti-inflammatory agents, and anesthetics.

Preparations for parenteral administration include sterile aqueous or non-aqueous solutions, suspensions, and emulsions. Parenteral vehicles include sodium chloride solution, Ringer's dextrose, dextrose and sodium chloride, lactated Ringer's, or fixed oils. Preservatives and other additives may also be present such as, for example, antimicrobials, antioxidants, chelating agents, and inert gases.

To aid dissolution of antibodies into the aqueous environment a surfactant might be added as a wetting agent. Surfactants may include anionic detergents such as sodium lauryl sulfate, dioctyl sodium sulfosuccinate and dioctyl sodium sulfonate. Cationic detergents might be used and could include benzalkonium chloride or benzethomium chloride. The list of potential nonionic detergents that could be included in the formulation as surfactants are lauromacrogol 400, polyoxyl 40 stearate, polyoxyethylene hydrogenated castor oil 10, 50 and 60, glycerol monostearate, polysorbate 20, 40, 60, 65 and 80, sucrose fatty acid ester, methyl cellulose and carboxymethyl cellulose. These surfactants could be present in the formulation of the protein or derivative either alone or as a mixture in different ratios. Additives which potentially enhance uptake of peptides are for instance the fatty acids oleic acid, linoleic acid and linolenic acid.

III. Methods

A. Therapeutic Administration

Methods are provided for treating cancer or an infection in a subject by administering to the subject a therapeutically effective amount of cell-penetrating anti-DNA antibodies. Also provided are methods of increasing a cell's radiosensitivity or chemosensitivity in a subject by administering to the subject a pharmaceutical composition containing cell-penetrating anti-DNA antibodies. In some embodiments, the method involves first selecting a subject that has been diagnosed with a neoplasm, such as a cancer or tumor, or an infection with a pathogen such as a virus.

The pharmaceutical composition may be administered in a number of ways depending on whether local or systemic treatment is desired, and on the area to be treated. For example, the compositions may be administered intravenously, intramuscularly, intrathecally, intraperitoneally, subcutaneously. The compositions may be administered directly into a tumor or tissue, e.g., stereotactically. In some embodiments, the compositions are administered into the brain or liver by injection or by a surgically implanted shunt.

The exact amount of the compositions required will vary from subject to subject, depending on the species, age, weight and general condition of the subject, the severity of the disorder being treated, and its mode of administration. Thus, it is not possible to specify an exact amount for every composition. However, an appropriate amount can be determined by one of ordinary skill in the art using only routine experimentation given the teachings herein. For example, effective dosages and schedules for administering the compositions may be determined empirically, and making such determinations is within the skill in the art. The dosage ranges for the administration of the compositions are those large enough to impair DNA repair in target cells and/or sensitize the target cells to radiotherapy and/or chemotherapy. The dosage should not be so large as to cause adverse side effects, such as unwanted cross-reactions, anaphylactic reactions, and the like. Generally, the dosage will vary with the age, condition, and sex of the patient, route of administration, whether other drugs are included in the regimen, and the type, stage, and location of the cancer to be treated. The dosage can be adjusted by the individual physician in the event of any counter-indications. Dosage can vary, and can be administered in one or more dose administrations daily, for one or several days. Guidance can be found in the literature for appropriate dosages for given classes of pharmaceutical products. A typical daily dosage of the antibody used alone might range from about 1 µg/kg to up to 100 mg/kg of body weight or more per day, depending on the factors mentioned above. In preferred embodiments, the antibody is present in amount from about 200 mg/m$^2$ to about 1000 mg/m$^2$, more preferably from about 200-900, 300-800, 400-700, 500-600 mg/m$^2$. In some embodiments, the unit dosage is in a unit dosage form for intravenous injection. In some embodiments, the unit dosage is in a unit dosage form for oral administration. In some embodiments, the unit dosage is in a unit dosage form for intratumoral injection.

The anti-DNA antibodies increase a cancer's radiosensitivity or chemosensitivity. Effective doses of chemotherapy and/or radiation therapy may be toxic for certain cancers. In some embodiments, the anti-DNA antibodies decrease the required effective dose of an anti-neoplastic drug or radiation levels needed to treat a cancer, thereby reducing toxicity of the effective dose. For example, the most commonly used dosage of doxorubicin is 40 to 60 mg/m$^2$ IV every 21 to 28 days, or 60 to 75 mg/m$^2$ IV once every 21 days. If the patient has a bilirubin level between 1.2 and 3 mg/dL, the dose should be reduced by 50%. If the patient has a bilirubin level between 3.1 and 5.0 mg/dL, the dose should be reduced by 75%. Serious irreversible myocardial toxicity leading to congestive heart failure often unresponsive to cardiac support therapy may be encountered as the total dosage of doxorubicin approaches 450 mg/m$^2$. When used in combination with the anti-DNA antibodies, doxorubicin dosage may be reduced to decrease myocardial toxicity without a loss in efficacy.

In other embodiments, the disclosed anti-DNA antibodies may be used with normal doses of drug or radiation to increase efficacy. For example, the anti-DNA antibodies may be used to potentiate a drug or radiation therapy for a cancer that is drug or radiation resistant. Cancers that are resistant to radiotherapy using standard methods include sarcomas, lymphomas, leukemias, carcinomas, blastomas, and germ cell tumors.

B. Screening Assay

Since anti-DNA antibodies are shown to inhibit DNA repair and increase radiosensitivity and/or chemosensitivity in cancer cells, a method of detecting anti-DNA antibodies in a sample is also provided. For example, the sample can be a bodily fluid containing antibodies, such as blood, serum, or plasma from a subject having, or suspected of having, SLE. The sample can be a tissue or cell sample, such as a biopsy.

In some embodiments, the method can be used to monitor the diagnosis or prognosis of a subject with SLE. For example, detection of cell penetrating anti-DNA antibodies can provide early detection of patients about to undergo an SLE flare-up.

In some embodiments, the method can be used to predict a subject's sensitivity to chemotherapy or radiotherapy. In these embodiments, the levels of cell penetrating anti-DNA antibodies in the sample can correspond to the level of sensitivity to chemotherapy or radiotherapy. In preferred embodiments, the chemotherapy is one that inhibits DNA repair or causes DNA damage.

The method can involve contacting cells with the sample from the subject and monitoring the effect of the sample on the cells. The cells are preferably a cell line, such as a cancer cell line, that has been shown to normally be radioresistant or chemoresistant but after treatment with anti-DNA antibodies, become radiosensitive and/or chemosensitive. In some embodiments, the cells are irradiated, and the method involves evaluating the effect of the sample on cell radiosensitivity. In other embodiments, the cells are contacted with an anti-neoplastic drug, and the method involves evaluating the effect of the sample on chemosensitivity. In still other embodiments, the method involves monitoring the direct effect of the sample on cell death. In all of these embodiments, an increase in radiosensitivity, chemosensitivity, or cell death, is an indication that the sample contains anti-DNA antibodies.

In other embodiments, the method involves an immunoassay, such as an ELISA or flow cytometry designed to detect anti-DNA antibodies. In preferred embodiments, the method is cell-based to detect cell penetration.

The present invention will be further understood by reference to the following non-limiting examples.

EXAMPLES

Example 1: A Cell-Penetrating Anti-DNA Antibody (3E10) Enhances Cellular Radiosensitivity In Vitro Materials and Methods Cell Lines:

MCF-7, HeLa, U251, and U87 cell lines were obtained from the American Type Culture Collection (ATCC). PEO1 and PEO1 C4-2 cells were obtained (Sakai W, et al. *Cancer Res* 69:6381 (2009)). Cells were grown and maintained in Dulbecco's Modification of Eagles Medium (DMEM; Mediatech®) supplemented with 10% fetal bovine serum (FBS) at 37° C. in 5% $CO_2$.

Production and Purification of 3E10 and 3E10 scFv:

3E10 was purified from hybridoma supernatant as described by Weisbart R H, et al. *J Immunol* 144; 2653 (1990). 3E10 scFv was expressed in *Pichia pastoris* and was purified from supernatant as described by Hansen J E, et al. *Brain Res* 1088:187 (2006). Protein concentrations were determined by Bradford assay.

In Vitro Cell Survival Assays:

Clonogenic assays and propidium iodide based assays were performed as described Hansen J E, et al. *Cancer Res* 67:1769 (2007); Stachelek G C, et al. *Cancer Res* 70:409 (2010)).

Cellular Irradiation:

Cells grown in 6- or 12-well plates were irradiated with x-rays at the doses specified using the X-RAD 320 Biological Irradiator (Precision X-Ray) in accordance with the manufacturer's instructions.

Table 1 presents data demonstrating that 3E10 scFv sensitizes MCF-7 and HeLa cells to IR. MCF-7 and Hela cells were irradiated in the presence of media containing control buffer or 3E10 scFv, and clonogenic survival was determined by colony formation assay. Surviving fraction±standard error of the mean relative to unirradiated control cells are presented for each treatment. Dose of 3E10 scFv was 0.25 µM for MCF-7 cells and 1.0 µM for HeLa cells. IR dose was 4 Gy for MCF-7 cells and 6 Gy for HeLa cells.

Results

SLE is an autoimmune disease characterized by aberrant production of autoantibodies reactive against host DNA (anti-nuclear antibodies; ANAs). A rare subset of these antibodies can penetrate into cells, but almost all are cytotoxic and inappropriate for clinical use (Alarcon-Segovia, D. *Lupus* 10:315 (2001)). However, one unusual cell-penetrating anti-DNA antibody, 3E10, isolated from a mouse model of SLE, was not found to be toxic to cells in culture or to mice in vivo, and was even shown to be safe in a Phase I human clinical trial evaluating the potential use of 3E10 in a vaccine to treat SLE (Spertini F, et al. *J Rheumatol* 26:2602 (1999); Weisbart R H, et al. *J Immunol* 144:2653 (1990); Zack D J, et al. *J Immunol* 157:2082 (1996)). 3E10 was not further pursued as a vaccine but was instead investigated as a molecular delivery vehicle (Hansen J E, et al. *Brain Res* 1088:187 (2006); Hansen J E, et al. *J Biol Chem* 282:20790 (2007)).

Besides its benign toxicity profile, 3E10 is further distinguished from other cell-penetrating ANAs by its mechanism of cellular penetration. Unlike all the others, cell penetration by 3E10 is independent of its Fc or constant domains; rather, the 3E10 single chain variable fragment (3E10 scFv) can, by itself, penetrate cells and localize in nuclei), in a mechanism mediated by an equilibrative nucleoside transporter that is ubiquitous on human cells (Hansen J E, et al. *J Biol Chem* 282:20790 (2007); Lisi S et al. *Clin Exp Med* 11:1 (2011)).

Both the full 3E10 antibody and 3E10 scFv have proven capable of delivering cargo proteins such as p53 and Hsp70 into cells in vitro and in vivo (Hansen J E, et al. *Brain Res* 1088:187 (2006); Hansen J E, et al. *Cancer Res* 67:1769 (2007); Zhan X, et al. *Stroke* 41:538 (2010)). "3E10 scFv" utilized in the experiments disclosed herein is the molecule described in Hansen J E, et al. *J Biol Chem* 282:20790 (2007), and citations referenced therein, which includes an antibody 3E10 VL domain linked to a 3E10 VH domain with a D31N mutation reported to enhance DNA binding and cell penetration. It was intended to use 3E10 to transport linked molecules with known radiosensitizing effects into cancer cells to enhance tumor response to radiotherapy. However, in initial experiments, it was discovered that 3E10, by itself, enhances cellular radiosensitivity. This is shown in Table 1 and FIG. 1B. Table 1 presents data demonstrating that 3E10 scFv sensitizes MCF-7 and HeLa cells to IR. MCF-7 and Hela cells were irradiated in the presence of media containing control buffer or 3E10 scFv, and clonigenic survival was determined by colony formation assay. Surviving fraction±standard error of the mean relative to unirradiated control cells are presented for each treatment. Dose of 3E10 scFv was 0.25 µM for MCF-7 cells and 1.0 µM for HeLa cells. IR dose was 4 Gy for MCF-7 cells and 6 Gy for HeLa cells.

Figure 1B:
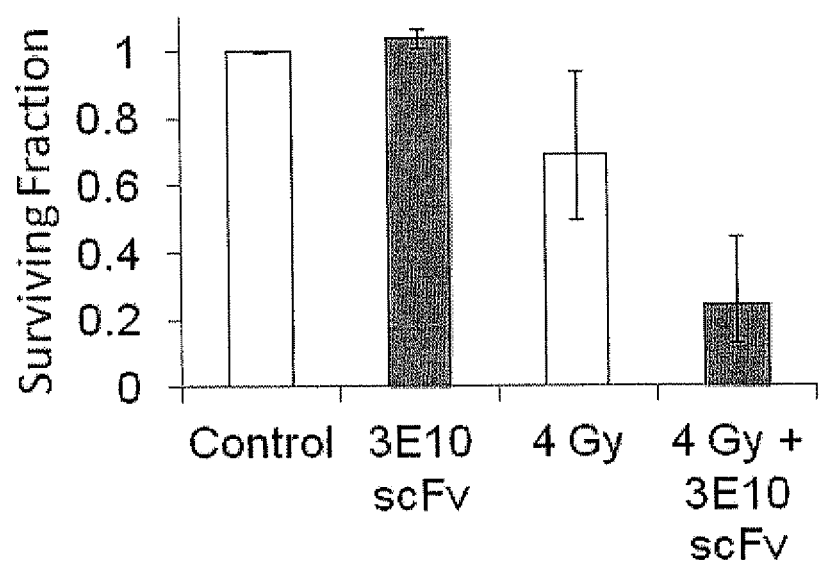
FIG. 1B is a bar graph showing clonogenic survival (surviving fraction relative to control) of U251 human glioma cells irradiated at 0 Gy (bars 1-2) or 4 Gy (bars 3-4) in the presence of control buffer (bars 1 and 3) or 10 μM 3E10 Fv (bars 2 and 4). Error bars represent standard error for replicate experiments.

FIG. 1B shows a clonogenic survival assay measuring the impact of 3E10 scFv on the survival of U251 human glioma cells treated with ionizing radiation (IR). U251 cells were incubated with growth media containing 3E10 scFv or control buffer for one hour, and cells were then irradiated with 0 or 4 Gy of IR and evaluated for clonogenicity by colony formation. Consistent with prior studies, the 3E10 scFv by itself was not toxic to unirradiated U251 cells. However, U251 cells irradiated in the presence of 3E10 scFv were found to be more sensitive to IR. 3E10 scFv also increased the radiosensitivity of MCF-7 human breast cancer cells and HeLa human cervical cancer cells at doses as low as 0.25 µM (Table 1). Radiosensitization by a cell-penetrating, anti-DNA antibody has not been previously described.

Example 2: A Cell-Penetrating Anti-DNA Antibody (3E10) Potentiates DNA-Damaging Chemotherapy In Vitro Materials and Methods Since radiation targets DNA, the impact of 3E10 on cancer cell response to DNA-damaging chemotherapy was tested. Specifically, the influence of 3E10 on cell sensitivity to doxorubicin versus paclitaxel, two agents commonly used in cancer therapy, was compared. Doxorubicin is an anthracycline antibiotic that intercalates into DNA and induces strand breaks (Tewey K M, et al. *Science* 226:466 (1984)), while paclitaxel interferes with microtubule function (Jordan M A, et al. *Proc Natl Acad Sci USA* 90:9552 (1993)) but does not directly damage DNA.

It was predicted that 3E10 scFv would sensitize cells to doxorubicin but not to paclitaxel. U87 human glioma cells were treated with increasing doses of doxorubicin (0-250 nM) or paclitaxel (0-25 nM) in the presence of control buffer or 10 µM 3E10 scFv, and percent cell killing was then determined by propidium iodide fluorescence one week after treatment.

Results

Figure 1C:
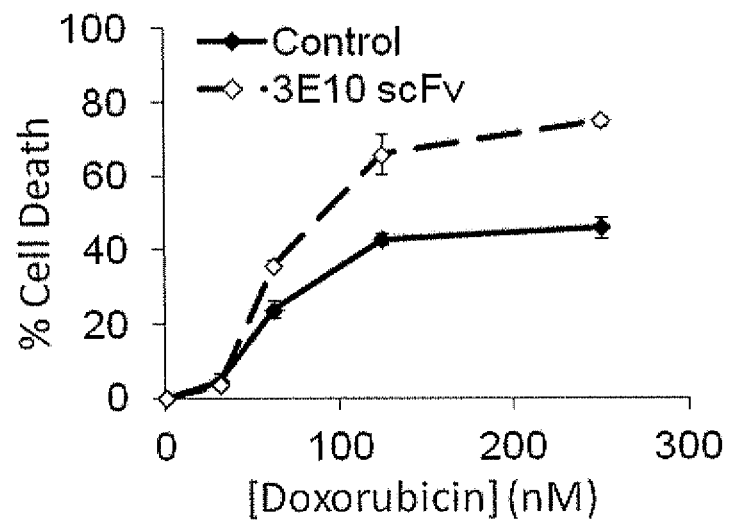
FIGS. 1C-1D are graphs showing cell death (%, measured by propidium iodide fluorescence) of U87 human glioma cells as a function of doxorubicin (Dox) (0-250 nM) (FIG. 1E) or paclitaxel (0-2.5 nM) (FIG. 1F) in the presence (dashed line) or absence (solid line) of 10 μM 3E10 scFv.
Figure 1D:
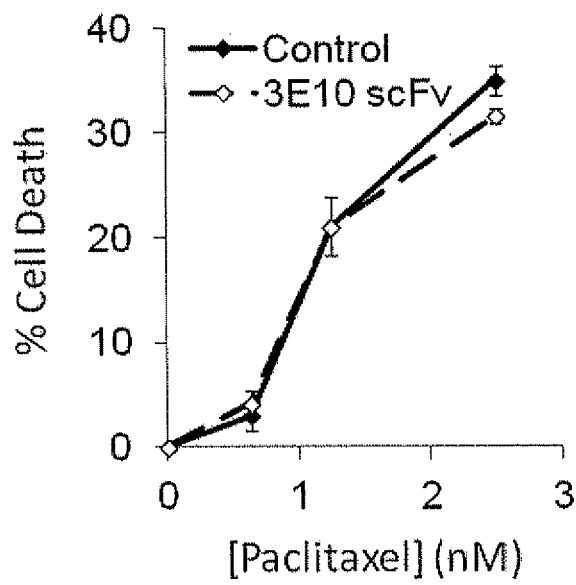

As predicted, 3E10 scFv significantly enhanced the sensitivity of the cells to doxorubicin but not to paclitaxel (FIGS. 1C and 1D). The ability of 3E10 scFv to sensitize cancer cells to both IR and doxorubicin but not to paclitaxel indicates that the antibody selectively potentiates cell killing by DNA-damaging therapies.

Example 3: A Cell-Penetrating Anti-DNA Antibody (3E10) Inhibits DNA Repair

Figure 2A:
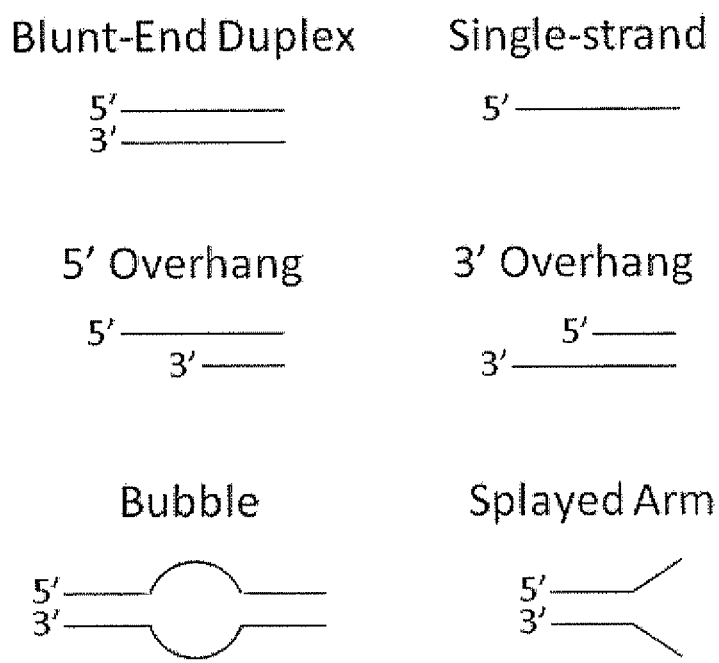
FIG. 2A demonstrates the different conformations of DNA substrates used in 3E10-DNA binding experiments.

Upon establishing that 3E10 scFv sensitizes cells to DNA-damaging agents, the mechanism underlying this effect was investigated. Both IR and doxorubicin induce DNA strand breaks, and so it was hypothesized that 3E10 scFv might have an effect on DNA repair, particularly strand break repair. As a first step, the DNA binding properties of 3E10 were examined. The binding affinity of 3E10 for several different DNA substrates, including single-stranded DNA, blunt-end duplex DNA, duplex DNA with an internal bubble due to heterology, duplex DNA with splayed single-stranded ends, duplex DNA with a 5' single-stranded tail, and duplex DNA with a 3' tail, (FIG. 2A) was determined by incubating radiolabeled DNA substrates prepared as described by Xu X, et al. *EMBO J* 28:568 (2009) with increasing concentrations of 3E10 (0-1 µM) followed by electrophoretic mobility shift analyses.

Materials and Methods

DNA Binding Studies:

Radiolabeled DNA substrates (single-stranded DNA, blunt-end duplex DNA, duplex DNA with an internal bubble due to heterology, duplex DNA with splayed single-stranded ends, duplex DNA with a 5' single-stranded tail, and duplex DNA with a 3' tail) were prepared as described by Xu X, et al. *EMBO J* 28:3005 (2009). Each substrate was incubated with 3E10 (0-10 µM) for 30 minutes at 4° C., followed by electrophoretic mobility shift analysis as described by Xu X, et al. *EMBO J* 28:3005 (2009). Kd was calculated by plotting percent oligonucleotide bound using ImageJ; National Institutes of Health versus concentration of 3E10.

DNA Repair Assays:

Single-strand break/base excision repair (BER) and RAD51-mediated strand exchange assays were performed as described by, respectively Stachelek G C, et al. *Cancer Res* 70:409 (2010); and Dray E, et al. *Proc Natl Acad Sci USA* 108:3560 (2011).

Microscopy:

Immunohistochemistry and γH2AX immunofluorescence were performed as previously described (Hansen J E, et al. *J Biol Chem* 282:20790 (2007); Stachelek G C, et al. *Cancer Res* 70:409 (2010)).

Results

Figure 2B:
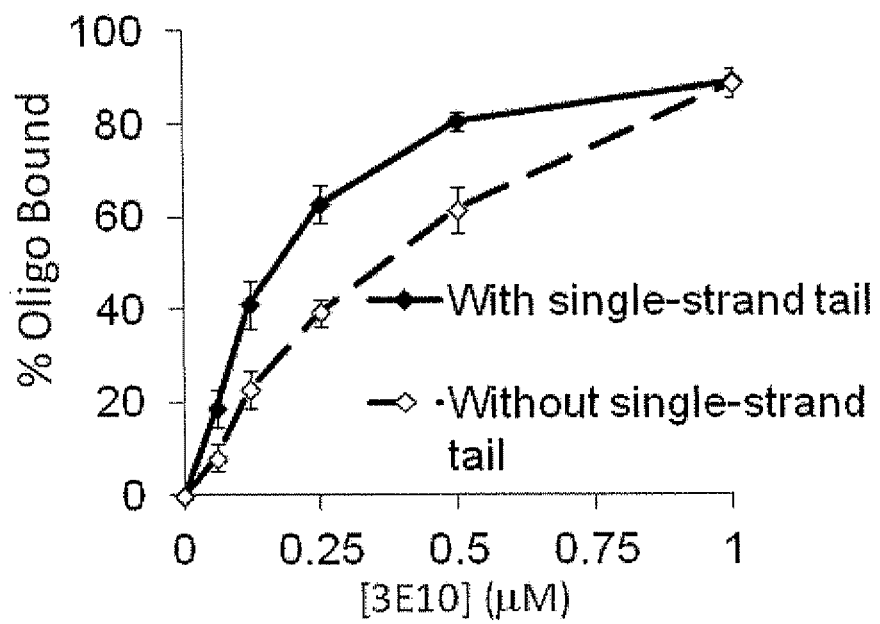
FIG. 2B is a graph showing fraction (%) of radiolabeled oligonucleotides with (solid line) or without (dashed line) free single-strand tail bound by 3E10 (determined by gel mobility shift analyses) after incubation with increasing concentrations of 3E10 (0-1 μM). These binding curves yield $K_d$s of 0.2 μM and 0.4 μM for 3E10 binding to substrates with and without a free single-strand end, respectively.
Figures 2C, 2D, 2E, 2F, 2G, 2H:
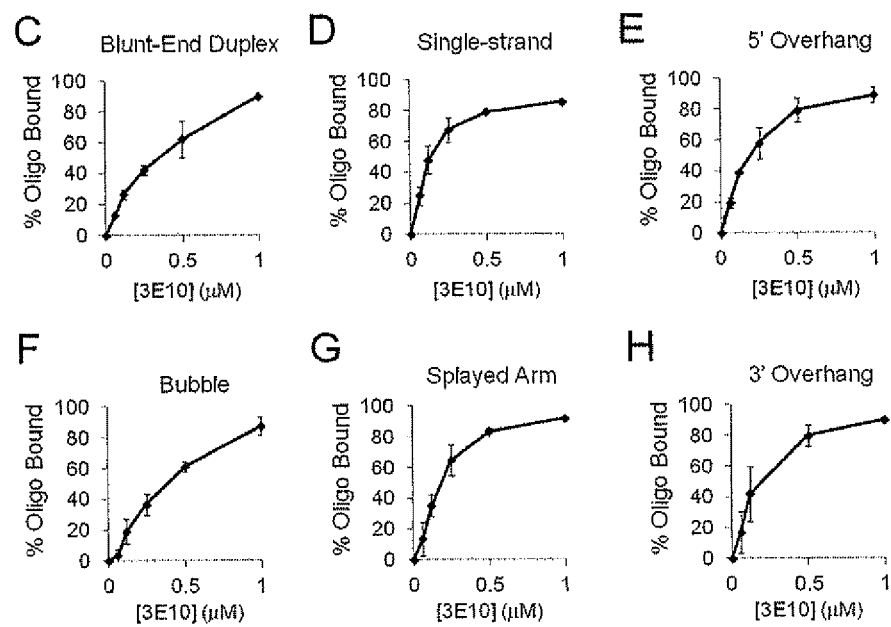
FIGS. 2C-2H present individual 3E10-DNA binding curves for each DNA conformation.

A left-shift in the binding curves for the single-strand, splayed arm, and 5'/3' tail substrates relative to those for the duplex and bubble substrates was observed, suggesting that 3E10 binds with greater affinity to substrates with free single-strand tails (FIGS. 2C-2H). The results were combined and plotted to directly compare the binding of 3E10 to substrates with or without a free single-strand tail. Overall, 3E10 bound to substrates with a free single-strand tail with a $K_d$ of 0.2 µM and to substrates without a free single-strand tail with a $K_d$ of 0.4 µM (FIG. 2B). These results suggest that upon cellular penetration and nuclear localization, 3E10 may preferentially bind to DNA repair or replication intermediates that consist of duplex DNA with single-stranded tails.

Figure 2I:
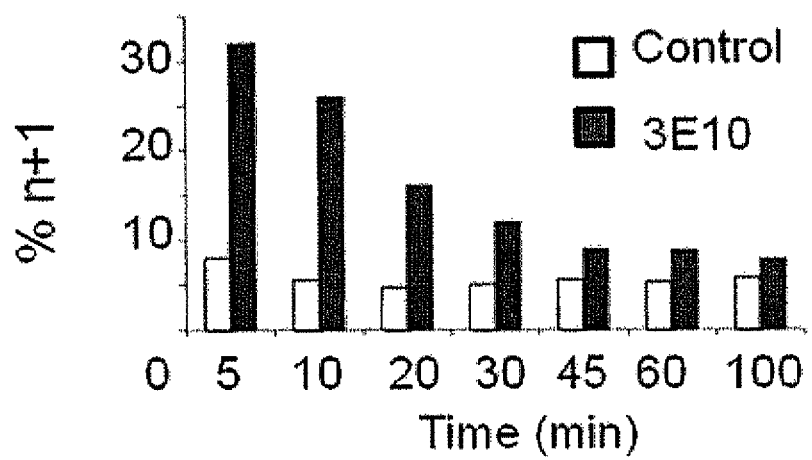
FIG. 2I is a bar graph showing single-strand break/base excision repair (BER) (% n+1 products represent the proportion of incompletely repaired intermediates in which a nucleotide has been added to a gapped duplex molecule but the remaining single strand break has not been repaired to yield a full length product) in synthetic radiolabeled duplex DNA substrates incubated with requisite repair enzymes in the presence of control buffer (open bars) or 20 μM E10 (solid bars). The repair reaction was stopped at the indicated time points, and the n, n+1, and duplex reaction products were quantified by gel electrophoresis and autoradiography.

The impact of 3E10 on specific DNA repair pathways was next examined, starting with an in vitro single-strand break/base excision repair (BER) assay (Stachelek G C, et al. *Cancer Res* 70:409 (2010)). In BER, a damaged base is excised by a glycosylase followed by cleavage of the phosphodiester backbone by an endonuclease to yield a substrate with a single-strand break (product n). The dRP lyase activity of DNA polymerase removes the dRP group, and its polymerase activity inserts the missing nucleotide and restores correct base pairing (product n+1). This is followed by ligation of the residual strand break by ligase to restore the integrity of the phosphodiester backbone, leading to conversion of the n+1 product into the full-length product in duplex conformation. The efficiency of BER may therefore be determined by tracking the levels of the n and n+0.1 species over time as quantified relative to the percentage of total substrate and product DNA. To measure the impact of 3E10 on BER, the repair of a mismatch in a radiolabeled DNA substrate (incubated with uracil DNA glycosylase, AP endonuclease, DNA polymerase β, and ligase) was tested in the presence of control buffer, control anti-tubulin antibody, or 3E10. 3E10 significantly delayed the conversion of the n+1 species to the final ligated product relative to the buffer control, suggesting that 3E10 impairs the ligation step of the single-strand break repair pathway (FIG. 2I). The anti-tubulin antibody had no effect on BER relative to control buffer.

Figure 3A:
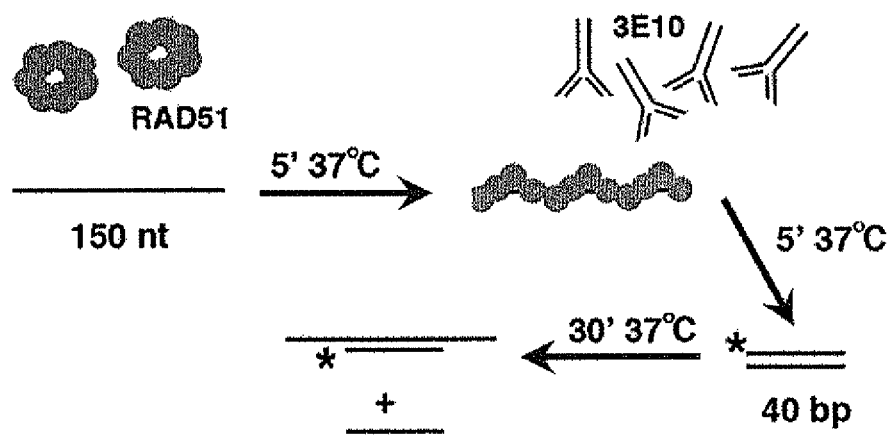
FIG. 3A is a schematic for an in vitro DNA strand exchange assay.
Figure 3B:
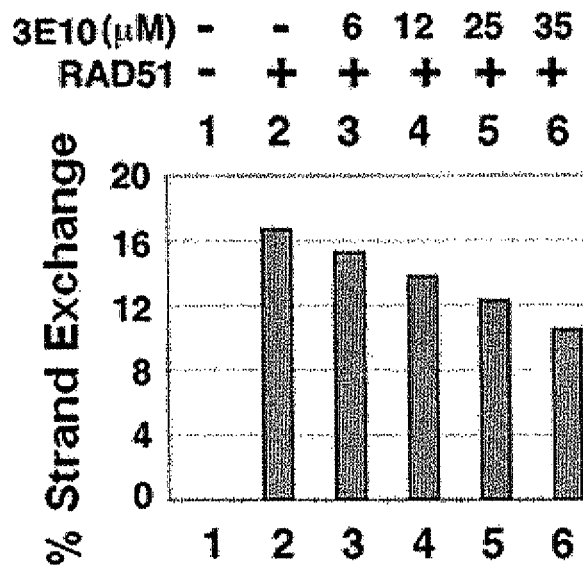
FIGS. 3B and 3C are bar graphs showing the impact of increasing dose of 3E10 (0-35 μM) on RAD51-mediated strand exchange using wild-type hRAD51 protein (FIG. 3B) or variant, hRAD51K133R (FIG. 3C). The hRAD51K133R-variant is even more active for strand exchange than the wild-type protein because it does not hydrolyze ATP. 3E10 inhibits strand exchange by both wild-type RAD51 and the hRAD51K133R variant. Immunofluorescence images demonstrate DNA double strand breaks (γH2AX foci) per U251 glioma cell 24 hours after irradiation with 2 Gy in the presence of control buffer or 10 μM E10 scFv.
Figure 3C:
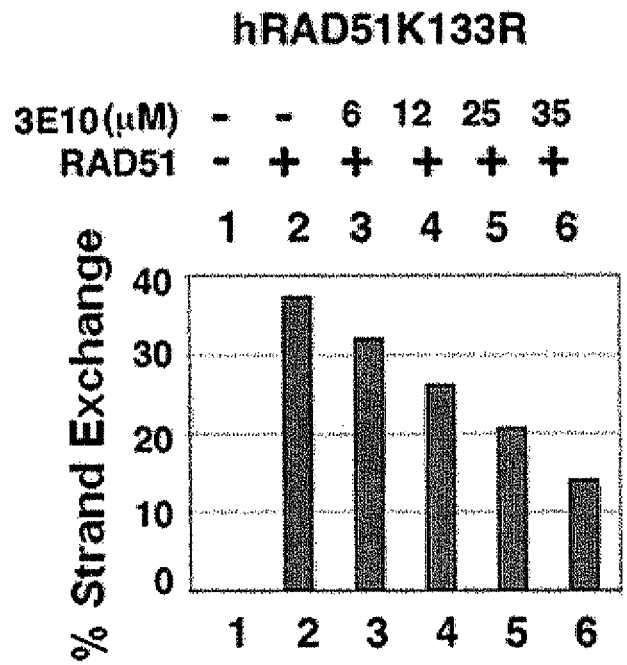
Figure 3D:
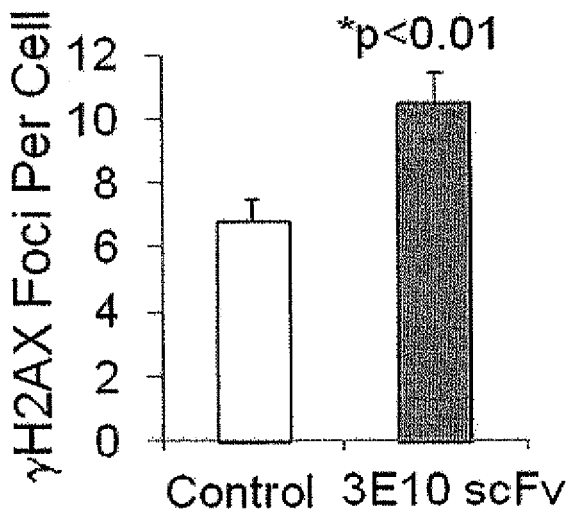
FIG. 3D is a bar graph showing the average number of DNA double strand breaks (γH2AX foci) per U251 glioma cell 24 hours after irradiation with 2 Gy in the presence of control buffer (open bar) or 10 μM 3E10 scFv (solid bar). Error bars represent standard errors.

To further probe the impact of 3E10 on DNA repair the effect of 3E10 on homology-dependent repair (HDR), a key pathway for the repair of DNA double-strand breaks (DSB), including IR-induced DSBs and DSBs associated with stalled replication forks, was tested (Arnaudeau C, et al. *J Mol Biol* 307:1235 (2001); Li X, et al. *Cell Res* 18:99 (2008)). HDR is dependent on the RAD51 recombinase, which binds single-strand DNA to form nucleofilaments that mediate strand invasion (Sung P, et al. *Science* 265:1241 (1994); Sung P, et al. *J Biol Chem* 278:42729 (2003); Sung P, et al. *Cell* 82:453 (1995)). Since 3E10 preferentially binds free single-strand tails it was hypothesized that the antibody might impair RAD51-mediated strand invasion and exchange. This hypothesis was tested in an in vitro strand exchange assay (Dray E, et al. *Proc Natl Acad Sci USA* 108:3560 (2011)), the schematic for which is shown in FIG. 3A. Purified human RAD51 (hRAD51) was incubated for 5 minutes with an unlabeled 150 bp single-stranded DNA substrate to allow formation of an hRAD51-single-stranded DNA nucleoprotein capable of strand invasion. 3E10 (0-35 µM) or a control anti-$His_6$ IgG antibody was next added to the reaction and allowed to incubate for 5 minutes. Next, a 40 bp DNA substrate in blunt end duplex conformation with one radiolabeled strand was added and allowed to incubate with the hRAD51-single-stranded DNA nucleoprotein filament in the presence or absence of antibody for 30 minutes (schematic shown in FIG. 3A). The degree of strand exchange was then visualized by electrophoresis and quantified. 3E10 inhibited strand exchange in a dose-dependent manner (FIG. 3B), while the control anti-$His_6$ IgG antibody had no impact on strand exchange. 3E10 was also able to suppress strand exchange mediated by a RAD51 variant, hRAD51K133R, that is defective in ATP hydrolysis and so is an even more potent mediator of strand exchange than wild-type RAD51 (Chi P, et al. *DNA Repair (Amst)* 5:381 (2006)) (FIG. 3C). These data demonstrate inhibition of HDR by 3E10 via suppression of RAD51-mediated strand exchange.

Since 3E10 was found to inhibit HDR in vitro, it was hypothesized that repair of DNA DSBs induced by DNA-damaging therapy would be delayed in cells treated with 3E10. To test this hypothesis, U251 glioma cells were treated with control buffer or 3E10 scFv (10 µM) and irradiated with 2 Gy of IR. Twenty-four hours later, the numbers of persisting DNA DSBs per cell were quantified by visualization of foci of the phosphorylated histone component, γH2AX, via immunofluorescence. Cells irradiated in the presence of 3E10 scFv showed an average of 10.5±1 γH2AX foci per cell at 24 hours, compared to 6.8±1 in cells irradiated in control buffer ($p<0.01$). These data demonstrate delayed resolution of DNA DSBs in cells treated with 3E10 scFv, in keeping with the in vitro results demonstrating inhibition of DNA repair by 3E10.

Example 4: A Cell-Penetrating Anti-DNA Antibody (3E10) is Synthetically Lethal to Cancer Cells Deficient in DNA Repair Materials and Methods Cancer cells harboring deficiencies in HDR due to BRCA2 mutations (Moynahan M E, et al. *Mol Cell* 7:263 (2001)) are highly vulnerable to killing by inhibition of single-strand break repair (Bryant H E, et al. *Nature* 434:913 (2005); Feng Z, et al. *Proc Natl Acad Sci USA* 108:686 (2011); Kaelin, Jr. W G, et al. *Nat Rev Cancer* 5:689 (2005)). Such inhibition can be achieved by treatment with inhibitors of poly(ADP-ribose) polymerase 1 (PARP-1) or DNA polymerase β, a phenomenon termed synthetic lethality (Stachelek G C, et al, *Cancer Res* 70:409 (2010); Bryant H E, et al. *Nature* 434:913 (2005); Kaelin, Jr. W G, et al. *Nat Rev Cancer* 5:689 (2005); Farmer H, et al. *Nature* 434:917 (2005)). In addition, BRCA2-deficient cells have been shown to be sensitive to further inhibition of HDR as shown by the synthetic lethal effect of knockdown of RAD52 in BRCA2-deficient cancer cells (Feng Z, et al. *Proc Natl Acad Sci USA* 108:686 (2011)). Based on the observation that 3E10 inhibits both single-strand break repair and HDR, it was hypothesized that 3E10 would be synthetically lethal to BRCA2-deficient cancer cells. To test this hypothesis, the impact of treatment with 3E10 scFv or the full 3E10 antibody on a matched pair of BRCA2-deficient (PEO1) and BRCA2-proficient (PEO1 C4-2) human ovarian cancer cells was evaluated (Sakai W, et al. *Cancer Res* 69:6381 (2009)). The impact of 3E10 scFv was also tested on BRCA2-proficient PEO4 human ovarian cancer cells and BRCA2-deficient CAPAN1/neo human pancreatic cancer cells.

Results

Figure 4A:
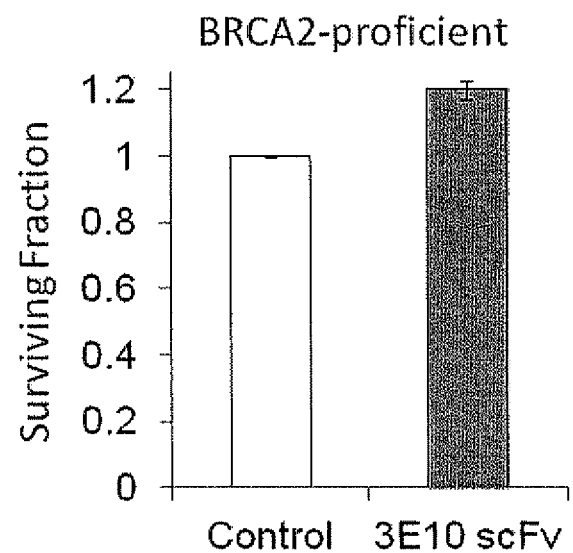
FIGS. 4A-4B are bar graphs showing clonogenic survival (surviving fraction relative to control) of BRCA2-proficient (FIG. 4A) or BRCA2-deficient (FIG. 4B) human ovarian cancer cells treated with control buffer (open bars) or 10 μM 3E10 scFv (solid bars) by colony formation measured 1-2 weeks following treatment.
Figure 4B:
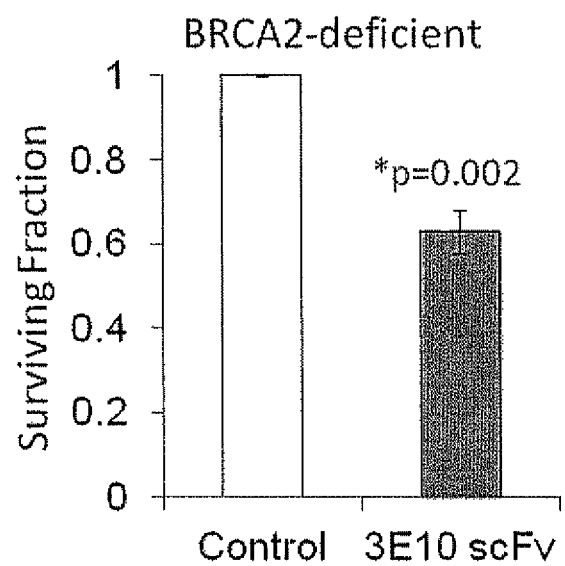
Figure 4C:
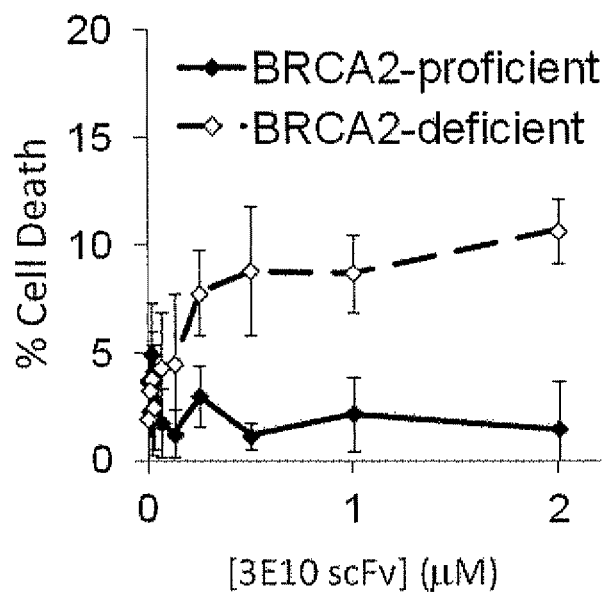
FIG. 4C is a graph showing % cell death of BRCA2-deficient (PEO1) and BRCA2-proficient (PEO4) human ovarian cancer cells treated with 3E10 scFv (0-2 μM). The impact of 3E10 scFv on cell survival was evaluated three days after treatment by CellTiterGlo® luminescence, which reports ATP levels as a measure of metabolically active cells. Error bars represent standard error of the mean of six measurements.
Figure 4D:
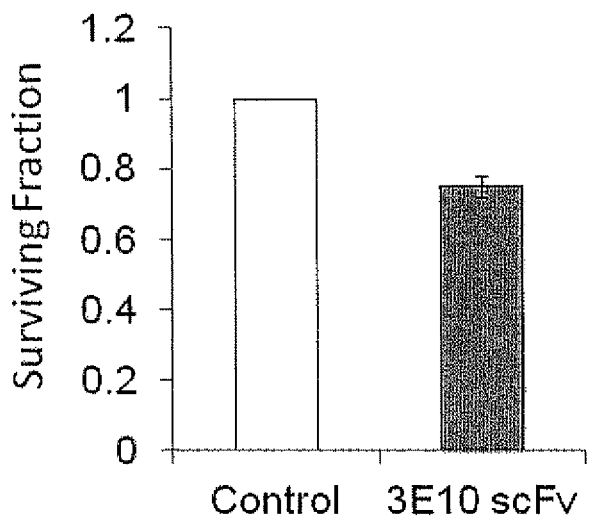
FIG. 4D is a graph showing the clonogenic survival (surviving fraction relative to control measured by colony formation) of BRCA2-deficient CAPAN1/neo cells (human pancreatic cancer cells) treated with control buffer or 3E10 scFv.
Figure 4E:
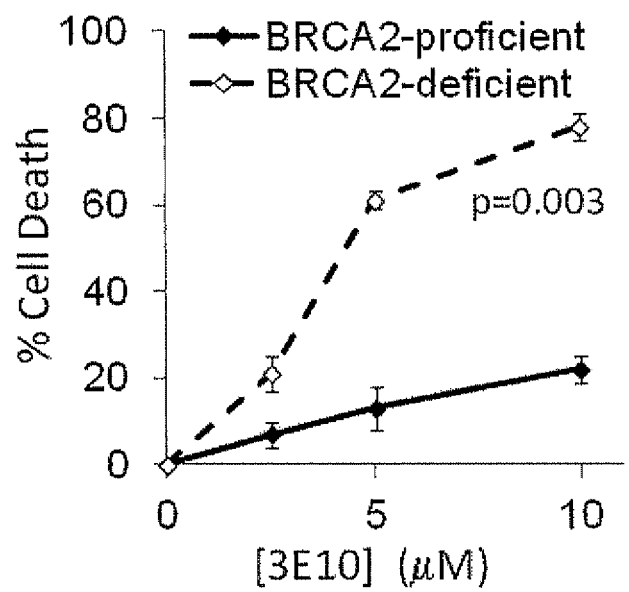
FIG. 4E is a graph showing cell death (%) of BRCA2-deficient (dashed line) or BRCA2-proficient (solid line) human ovarian cancer cells treated with 0 μM, 2.5 μM, 5 μM, or 10 μM of the full 3E10 antibody.

3E10 scFv TREATMENT reduced the clonogenic survival of the BRCA2-deficient PEO1 cells ($p=0.03$) but did not adversely impact the survival of the BRCA2-proficient PEO1 C4-2 cells (FIG. 4A-4B). 3E10 scFv was also toxic to BRCA2-deficient PEO1 cells but BRCA2-proficient PEO4 cells in a cell-viability assay (FIG. 4C). 3E10 scFv alone was also toxic to BRCA2-deficient human pancreatic cancer cells (CAPAN1/neo) (FIG. 4D). The full 3E10 antibody was similarly selectively toxic to the BRCA2-deficient PEO1 cells in a dose-dependent manner (FIG. 4E). These data provide the first evidence for a synthetic lethal effect of a cell-penetrating anti-DNA antibody on cancer cells deficient in DNA repair and demonstrate the potential utility of 3E10 as a targeted cancer therapy for malignancies with DNA repair deficiencies. Importantly, the synthetic lethal effect of 3E10 on BRCA2-deficient cancer cells is in keeping with the mechanistic experiments described above showing that 3E10 impacts DNA strand break repair.

In addition, hypoxic cancer cells have been shown to have reduced homology=directed repair capacity (Bindra, et al. Mol. Cell. Biol. 24(19):8504-8518 (2004)), so 3E10 and similar antibodies are expected to be synthetically lethal to cancer cells that are hypoxic.

Example 5: A Cell-Penetrating Anti-DNA Antibody, 3E10, Profoundly and Selectively Sensitizes DNA-Repair Deficient Cancer Cells to DNA-Damaging Therapy Materials and Methods In order to determine whether 3E10 would have an even greater impact on BRCA2-deficient cancer cells when coupled with a DNA-damaging agent, BRCA2-deficient PEO1 and BRCA2-proficient PEO1 C4-2 ovarian cancer cells were treated with control buffer, 10 µM 3E10, 3 nM doxorubicin, or 10 µM 3E10+3 nM doxorubicin. Percent cell death was then evaluated by propidium iodide fluorescence three days after treatment. A low dose of doxorubicin (3 nM) was selected to minimize the effect of doxorubicin alone on the cells, and the decision to measure percent cell death 3 days after treatment was made in order to minimize the confounding effects of synthetic lethality by 3E10 alone on BRCA2-deficient cells, which is evident approximately seven days post-treatment.

Results

Figure 4F:
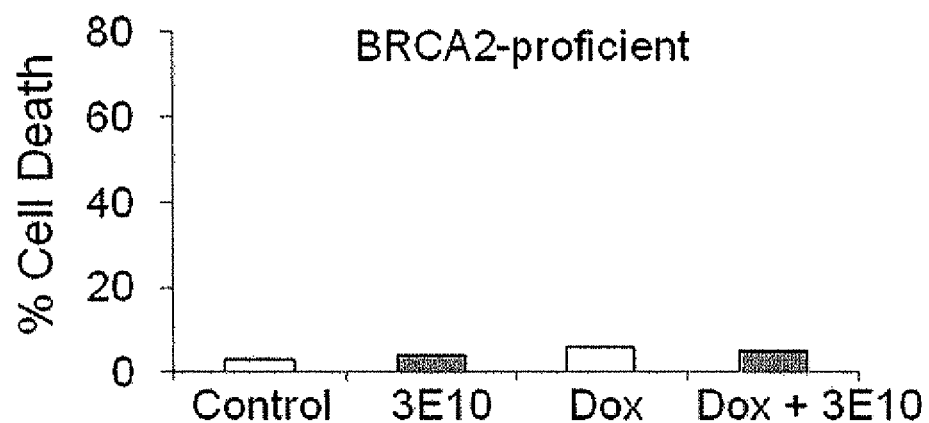
FIGS. 4F and 4G are bar graphs showing cell death (%) of BRCA2-deficient (FIG. 4G) or BRCA2-proficient (FIG. 4F) human ovarian cancer cells treated with control buffer (bar 1), 10 μM 3E10 (bar 2), 3 nM doxorubicin (Dox) (bar 3), or 10 μM 3E10+3 nM doxorubicin (bar 4).
Figure 4G:
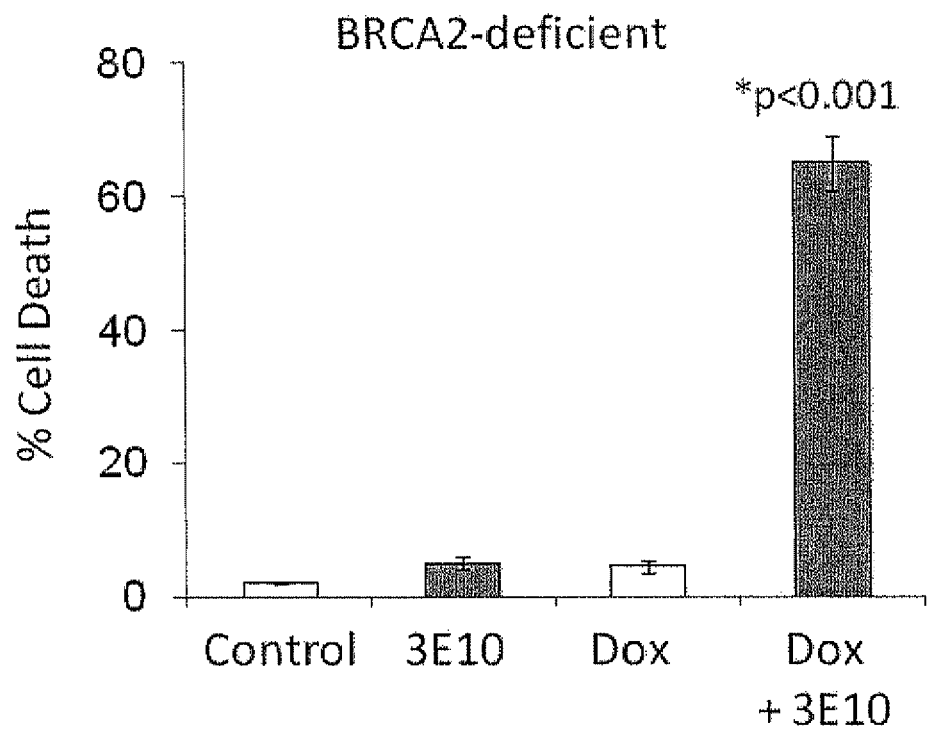

As expected, the low dose of doxorubicin alone was not significantly toxic to BRCA2-proficient or BRCA2-deficient cells. The addition of 3E10 to the doxorubicin had a minimal impact on the BRCA2-proficient cells. However, the combination of 3E10 and doxorubicin was highly cytotoxic to BRCA2-deficient cells (65%±7 cell death, p<0.001) (FIG. 4F-4G).

Example 6: 3E10 Potentiates DNA-Damaging Chemotherapy In Vivo

It was next determined whether the impact of 3E10 on tumor cell sensitivity to DNA-damaging therapy is preserved in vivo in a mouse tumor model.

Materials and Methods

The full 3E10 antibody was used for in vivo studies due to its expected greater half-life in the circulation compared to the variable fragment. U87 glioma tumors were generated in SCID mice by subcutaneous injection. When tumors had formed and were in a consistent growth phase, mice were treated by intraperitoneal injection of control buffer, 3E10 antibody alone (0.8 mg in 0.5 mL PBS, 10 μM), doxorubicin alone (80 μg/kg), or both 3E10 and doxorubicin. Each treatment group was composed of 4 mice. The impact of treatment was then evaluated by measuring tumor growth three days after injection. The selection of this time point for tumor measurement was based on the in vitro studies that demonstrated that the antibody's impact on cancer cell sensitivity to doxorubicin can be detected 3 days after treatment. Additional tumor measurements after 3 days could not be obtained due to predetermined institutional requirements for animal sacrifice when tumors reached a volume of 400 mm$^3$, which was rapidly achieved in the control groups.

Results

Figure 5:
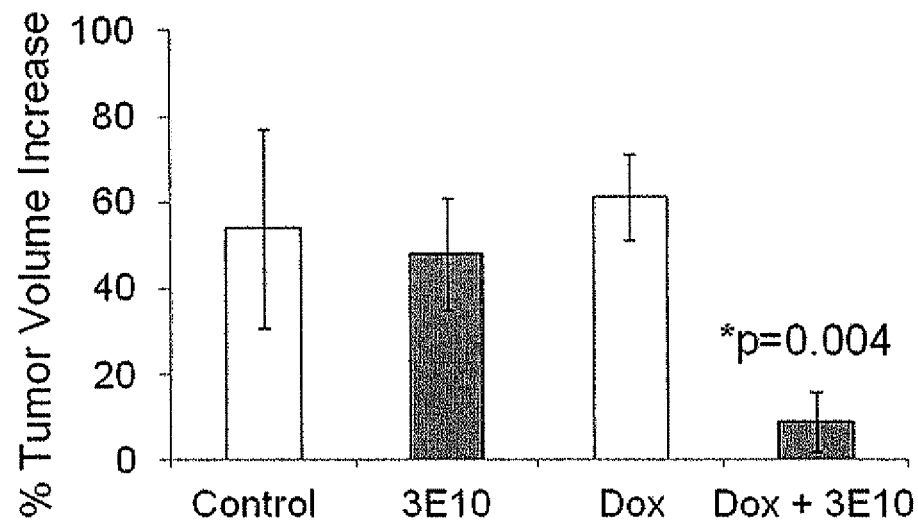
FIG. 5 is a bar graph showing tumor volume (% increase) of U87 glioma tumors generated in SCID mice by subcutaneous injection treated by intraperitoneal injection of control buffer (bar 1), 3E10 antibody alone (0.8 mg in 0.5 mL PBS, 10 μM) (bar 2), doxorubicin (Dox) alone (80 μg/kg) (bar 3), or both 3E10 and doxorubicin (bar 4). Each treatment group was composed of 4 mice. The impact of treatment was evaluated by measuring tumor growth three days after injection.

Tumors in mice treated with control buffer increased in volume by 54%±23. Treatment with 3E10 or doxorubicin alone did not significantly impact tumor growth, with tumor volumes increased by 48%±13 and 61%±10, respectively. By contrast, tumor growth was significantly reduced in mice treated with combined 3E10 and doxorubicin, with tumors increased in size by only 9%±7 (p=0.004, with p calculated by comparison of absolute tumor volumes in mice treated with doxorubicin+3E10 versus doxorubicin alone). These data demonstrate sensitization of tumors to doxorubicin by 3E10 in vivo (FIG. 5).

Figure 6A:
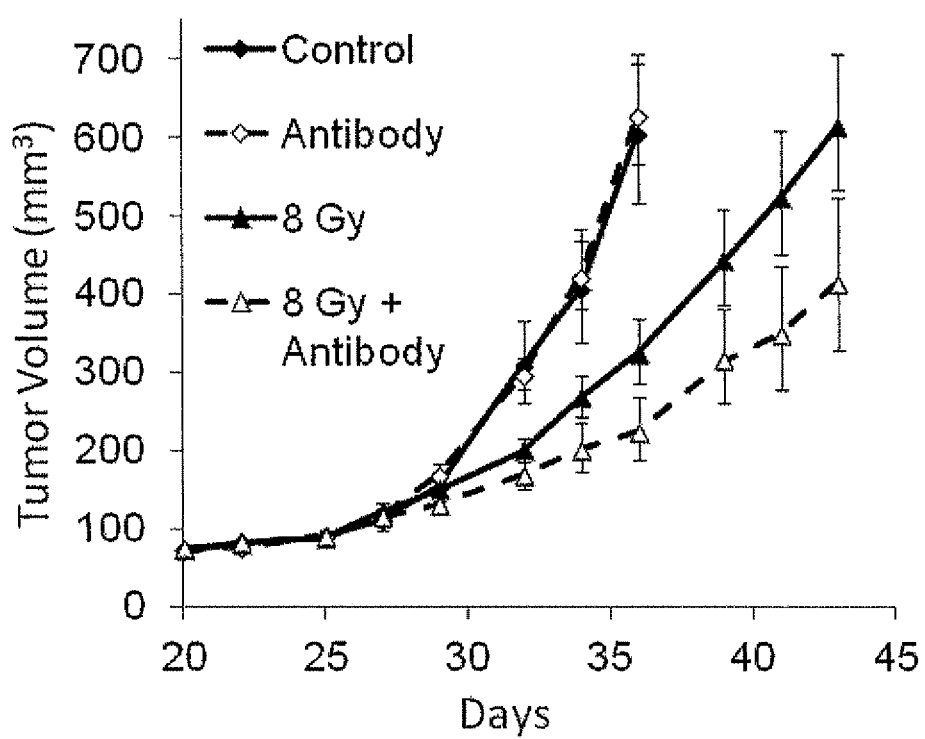
FIG. 6A is a graph showing tumor volume (mm$^3$) as a function of time (days) of human glioma xenograft mice treated with intraperitoneal injection of control PBS buffer (solid diamonds and triangles) or 3E10 (1 mg in PBS) (open diamonds and triangles) twenty-six days after U87 cell implantation (tumors had grown to a mean size of approximately 100 mm$^3$), again 24 hours later, and then irradiated with 0 Gy (diamonds) or 8 Gy (triangles) 2 hours after the second injection.

Example 7: A Cell-Penetrating Anti-DNA Antibody (3E10) Sensitizes Human Glioma Xenografts to Ionizing Radiation In Vivo Materials and Methods Human glioma xenografts were generated by subcutaneous injection of U87 cells into the flanks of nude mice. Treatment groups were: Control (n=8); Antibody (n=8), 8 Gy (of ionizing radiation) (n=8), and 8 Gy+Antibody (n=7; one animal lost in anesthesia). Twenty-five days after implantation, tumors had grown to a mean size of ~100 mm$^3$ mice. On day 26 the mice were treated with intraperitoneal injection of control buffer (PBS; "Control" and "8 Gy" groups) or 3E10 (1 mg in PBS; "Antibody" and "8 Gy+Antibody" groups). Each group then received a second injection of the same reagent 24 hours later. 2 hours after the second injection tumors in the "8 Gy" and "8 Gy+Antibody" groups were irradiated with 8 Gy. Tumor volumes in each group were then followed and mice were sacrificed when tumor volume reached 1000 mm$^3$. Tumor growth measurements versus days after tumor implantation are shown in FIG. 6A.

Results

3E10 alone (open diamonds) had no significant impact on tumor growth relative to control buffer alone (solid diamonds). However, the combination of 3E10 and 8 Gy (open triangles) suppressed tumor growth to a greater degree than 8 Gy alone (solid triangles).

Figure 6B:
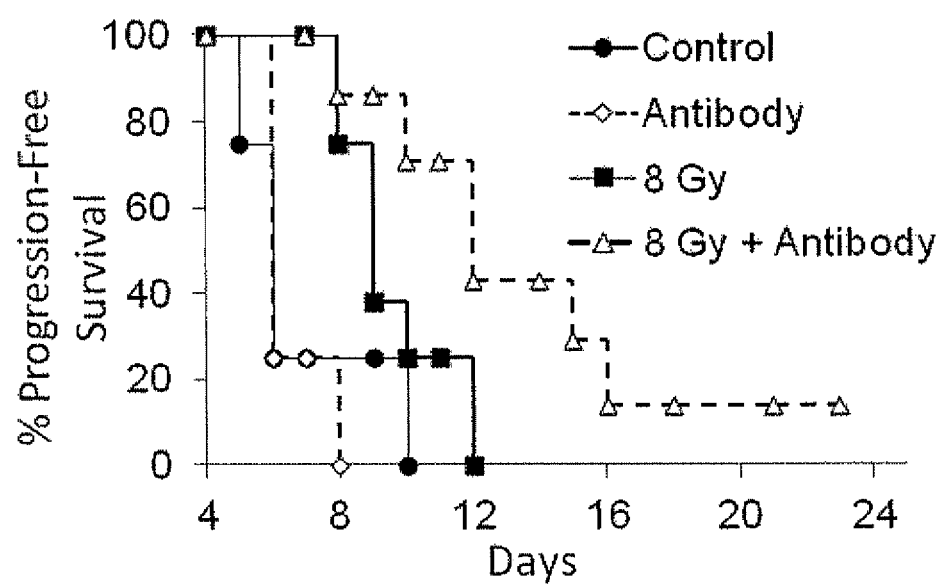
FIG. 6B presents Kaplan-Meier plots of progression-free survival in each group. Progression-free survival is defined as survival with tumor not having increased in size by threefold or greater relative to baseline size. Baseline size is defined as tumor size one day prior to antibody treatment, which is represented as day 25 in FIG. 6A and day 0 in FIG. 6B. Tumor tripling time (time required for tumors to increase in volume threefold over baseline) was 9.5±0.5 days in tumors treated with 8 Gy as compared to 13.7±1.8 days in tumors treated with 8 Gy+3E10 (p=0.04). 3E10 alone, however, had no impact on U87 tumors relative to control buffer alone, with tumor tripling time of control tumors 6.8±0.7 days versus 6.5±0.3 days in tumors treated with 3E10 alone (p=0.67).

In FIG. 6B, Kaplan-Meier plots of progression-free survival in each group are presented. Progression-free survival is defined as survival with tumor not having increased in size by threefold or greater relative to baseline size. Baseline size is defined as tumor size one day prior to antibody treatment, which is represented as day 25 in panel A and day 0 in panel B. Tumor tripling time (time required for tumors to increase in volume threefold over baseline) was 9.5±0.5 days in tumors treated with 8 Gy as compared to 13.7±1.8 days in tumors treated with 8 Gy+3E10 (p=0.04). 3E10 alone, however, had no impact on U87 tumors relative to control buffer alone, with tumor tripling time of control tumors 6.8±0.7 days versus 6.5±0.3 days in tumors treated with 3E10 alone (p=0.67). These data demonstrate sensitization of human glioma xenografts to ionizing radiation by 3E10 in vivo. Error bars represent standard error of the mean.

We claim:

1. A method of inhibiting DNA repair in neoplastic or virally transforming or virally transformed cells in a subject, comprising administering to the neoplastic, virally transforming or virally transformed cells in the subject a pharmaceutical composition comprising an effective amount of anti-DNA unconjugated antibodies or antigen binding fragments thereof to impair a DNA repair pathway, wherein all of the anti-DNA unconjugated antibodies or antigen binding fragments thereof of the pharmaceutical composition consist of one or more cell penetrating unconjugated monospecific anti-DNA antibodies or cell penetrating unconjugated antigen binding fragments thereof, wherein the cell penetrating unconjugated monospecific anti-DNA antibodies or cell penetrating unconjugated antigen binding fragments thereof consist of monoclonal antibody 3E10 produced by ATCC Accession No. PTA 2439 hybridoma, or a cell penetrating antigen binding fragment or humanized form thereof.

2. The method of claim 1, wherein the neoplastic cells are cancer cells selected from the group consisting of sarcomas, lymphomas, leukemias, carcinomas and adenocarcinomas, blastomas, germ cell tumors, gliomas, neuroendocrine tumors, melanomas, rhabdoid tumors, embryonal tumors, neuroectodermal tumors, carcinoid tumors, craniopharyngiomas, histiocytomas, medulloepitheliomas, mesotheliomas, multiple myelomas, chronic myeloproliferative disease, primitive neuroectodermal tumors, salivary gland tumors, thymomas, thymic carcinoma, thyroid cancer, and Wilms tumor.

3. The method of claim 1, wherein the cells are radiation resistant.

4. The method of claim 1, wherein the cells are resistant to chemotherapy.

5. The method of claim 1, wherein the cells have intrinsic defective or deficient DNA repair.

6. The method of claim 1, wherein the virally transforming or virally transformed cells are exposed to or infected with a virus having or causing DNA repair defects or deficiencies, or is dependent on host DNA repair pathways for infection, integration, or replication.

7. The method of claim 6, wherein the virally transforming or virally transformed cells are exposed to or infected with a lentivirus.

8. The method of claim 1, wherein the cells have one or more mutations in or abnormal expression of DNA repair genes selected from the group consisting of XRCC1, ADPRT (PARP-1), ADPRTL2, (PARP-2), POLYMERASE BETA, CTPS, MLH1, MSH2, FANCD2, PMS2, p53, p21, PTEN, RPA, RPA1, RPA2, RPA3, XPD, ERCC1, XPF, WS19, RAD51, RAD51b, RAD51C, RAD51D, DMC1, XRCCR, XRCC3, BRCA1, BRCA2, PALB2, RAD52, RAD54, RAD50, MRE11, NB51, WRN, BLM, KU70, KU80, ATM, ATR CHK1, CHK2, FANCA, FANCB, FANCC, FANCD1, FANCD2, FANCE, FANCF, FANCG, FANCC, FANCD1, FANCD2, FANCE, FANCF, FANCG, RAD1, and RAD9.

9. The method of claim 1, wherein the cells have a defective tumor suppressor gene such as BRCA1 or BRCA2.

10. The method of claim 1, wherein the cells are part of a hypoxic tumor.

11. The method of claim 1, wherein the antibodies are administered to the subject in combination with a radiosensitizer.

12. The method of claim 11, wherein the radiosensitizer is selected from the group consisting of cisplatin, doxorubicin, gemcitabine, 5-fluorouracil, PARP1 inhibitors, histone deacetylase inhibitors, proteasome inhibitors, epidermal growth factor receptor (EGRF) inhibitors, insulin-like growth factor-1 (IGF-1) receptor inhibitors, CHK1 inhibitors, mTOR inhibitors, kinase inhibitors, pentoxifylline, and vinorelbine.

13. The method of claim 1, further comprising treating the subject with radiation therapy, wherein the cell-penetrating anti-DNA antibodies increase the cells' sensitivity to radiation therapy.

14. The method of claim 1, further comprising treating the subject with an antineoplastic drug that damages DNA or inhibits DNA repair, wherein the cell-penetrating anti-DNA antibodies increase the cells' sensitivity to the antineoplastic drug.

15. The method of claim 1, further comprising treating the subject with a therapeutic monoclonal antibody.

16. The method of claim 1, wherein the cell-penetrating anti-DNA antibodies are derived from a subject with an autoimmune disease.

17. The method of claim 16, wherein the autoimmune disease is systemic lupus erythematous, or an animal model thereof.

18. The method of claim 1, wherein the cell-penetrating anti-DNA antibodies or antigen binding fragments thereof consist of a single chain variable fragment of the monoclonal antibody 3E10 produced by ATCC Accession No. PTA 2439 hybridoma or a humanized form thereof.

19. The method of claim 1, wherein the cell-penetrating anti-DNA antibodies or antigen binding fragments thereof are transported into the nucleus of the cell without the aid of a carrier or conjugate.

20. The method of claim 1, wherein administering the antibodies or antigen binding fragments thereof in combination with chemotherapy or radiation therapy increases DNA damage in the neoplastic or virally transforming or virally transformed cells caused by the radiation or chemotherapy relative to administering of the radiation or chemotherapy alone.

21. The method of claim 1, wherein the antibodies or antigen binding fragments thereof are not directly cytotoxic to DNA repair-proficient cells.

22. The method of claim 21, wherein the antibodies or antigen binding fragments are synthetically lethal to DNA repair-deficient cells.

23. A method of treating a subject with cancer, comprising administering to the subject a pharmaceutical composition comprising an effective amount of anti-DNA antibodies or antigen binding fragments thereof to impair a DNA repair pathway in cancer cells in the subject, wherein all of the anti-DNA unconjugated antibodies or antigen binding fragments thereof of the pharmaceutical composition consist of one or more cell penetrating unconjugated monospecific anti-DNA antibodies or cell penetrating unconjugated antigen binding fragments thereof,
   wherein the cell penetrating unconjugated monospecific anti-DNA antibodies or antigen binding fragments thereof consist of monoclonal antibody 3E10 produced by ATCC Accession No. PTA 2439 hybridoma, or a cell penetrating unconjugated antigen binding fragments or humanized form thereof.

24. The method of claim 23, further comprising administering to the subject a DNA damaging agent.

25. The method of claim 24, wherein the DNA damaging agent is a chemotherapeutic drug or radiation.

26. The method of claim 23, wherein the subject comprises cancer cells that are DNA repair-deficient.

27. The method of claim 26, wherein the DNA repair-deficient cells are BRCA1 or BRCA2 deficient.

28. The method of claim 23, wherein the cell-penetrating anti-DNA antibodies or antigen binding fragments thereof consist of a single chain variable fragment of the monoclonal antibody 3E10 produced by ATCC Accession No. PTA 2439 hybridoma or a humanized form thereof.

29. The method of claim 1, wherein the pharmaceutical composition comprises an effective amount of the unconjugated cell-penetrating anti-DNA antibodies or antigen binding fragments thereof to reduce DNA repair.

30. The method of claim 23, wherein the pharmaceutical composition comprises an effective amount of the unconjugated cell-penetrating anti-DNA antibodies or antigen binding fragments thereof to reduce DNA repair.

31. The method of claim 1, wherein the cell-penetrating anti-DNA antibodies or antigen binding fragments thereof comprise a divalent single-chain variable fragment (discFv) of the monoclonal antibody 3E10 produced by ATCC Accession No. PTA 2439 hybridoma, or humanized form thereof.

32. The method of claim 23, wherein the cell-penetrating anti-DNA antibodies or antigen binding fragments thereof comprise a divalent single-chain variable fragment (discFv) of the monoclonal antibody 3E10 produced by ATCC Accession No. PTA 2439 hybridoma, or humanized form thereof.

* * * * *